(12) United States Patent
Sawhney et al.

(10) Patent No.: US 7,790,192 B2
(45) Date of Patent: ***Sep. 7, 2010

(54) APPARATUS AND METHODS FOR SEALING A VASCULAR PUNCTURE

(75) Inventors: Amarpreet S. Sawhney, Lexington, MA (US); Farhad Khosravi, Los Altos Hills, CA (US); Suresh S. Pai, Mountain View, CA (US)

(73) Assignee: AccessClosure, Inc., Mountain View, CA (US)

( * ) Notice: Subject to any disclaimer, the term of this patent is extended or adjusted under 35 U.S.C. 154(b) by 1631 days.

This patent is subject to a terminal disclaimer.

(21) Appl. No.: 10/982,387

(22) Filed: Nov. 5, 2004

(65) Prior Publication Data

US 2006/0034930 A1 Feb. 16, 2006

(51) Int. Cl.
*A61F 2/04* (2006.01)
(52) U.S. Cl. ....................................................... 424/423
(58) Field of Classification Search ....................... None
See application file for complete search history.

(56) References Cited

U.S. PATENT DOCUMENTS

| | | | |
|---|---|---|---|
| 2,115,492 A | 4/1938 | Kober |
| 3,765,419 A | 10/1973 | Usher |
| 4,002,173 A | 1/1977 | Manning |
| 4,260,077 A | 4/1981 | Schroeder |
| 4,327,709 A | 5/1982 | Hanson et al. |
| 4,362,150 A | 12/1982 | Lombardi, Jr. et al. |
| 4,472,542 A | 9/1984 | Nambu |
| 4,540,404 A | 9/1985 | Wolvek |
| 4,655,211 A | 4/1987 | Sakamoto et al. |
| 4,664,857 A | 5/1987 | Nambu |
| 4,734,097 A | 3/1988 | Tanabe |
| 4,738,658 A | 4/1988 | Magro et al. |
| 4,838,280 A | 6/1989 | Haaga |

(Continued)

FOREIGN PATENT DOCUMENTS

EP 0 476 178 A1 3/1992

(Continued)

OTHER PUBLICATIONS

PCT International Search Report for PCT/USUS2005/039692, Applicant Accessclosure, Inc., Form PCT/ISA/210 and 220, dated Mar. 21, 2006 (6 pages).

(Continued)

*Primary Examiner*—Carlos A Azpuru
(74) *Attorney, Agent, or Firm*—William A. English; Vista IP Law Group LLP

(57) ABSTRACT

Apparatus for sealing a puncture communicating with a blood vessel includes a porous carrier formed from lyophilized hydrogel or other material. The plug may include at least first and second hydrogel precursors and a pH adjusting agent carried by the porous carrier in an unreactive state prior to exposure to an aqueous physiological environment. Once exposed to bodily fluids, the carrier expands as the lyophilized material hydrates to enhance and facilitate rapid hemostasis of the puncture. When the plug is placed into the puncture, the natural wetting of the plug by bodily fluids (e.g., blood) causes the first and second precursors to react and cross-link into an adhesive or "sticky" hydrogel that aids in retaining the plug in place within the puncture.

23 Claims, 14 Drawing Sheets

U.S. PATENT DOCUMENTS

| | | |
|---|---|---|
| 4,852,568 A | 8/1989 | Kensey |
| 4,890,612 A | 1/1990 | Kensey |
| 5,061,274 A | 10/1991 | Kensey |
| 5,104,375 A | 4/1992 | Wolf et al. |
| 5,104,389 A | 4/1992 | Deem et al. |
| 5,108,421 A | 4/1992 | Fowler |
| 5,192,300 A | 3/1993 | Fowler |
| 5,192,302 A | 3/1993 | Kensey et al. |
| 5,221,259 A | 6/1993 | Weldom et al. |
| 5,258,042 A | 11/1993 | Mehta |
| 5,259,835 A | 11/1993 | Clark et al. |
| 5,275,616 A | 1/1994 | Fowler |
| 5,290,310 A | 3/1994 | Makower et al. |
| 5,292,332 A | 3/1994 | Lee |
| 5,306,254 A | 4/1994 | Nash et al. |
| 5,320,639 A | 6/1994 | Rudnick |
| 5,324,306 A | 6/1994 | Makower et al. |
| 5,334,216 A | 8/1994 | Vidal |
| 5,383,896 A | 1/1995 | Gershony et al. |
| RE34,866 E | 2/1995 | Kensey et al. |
| 5,391,183 A | 2/1995 | Janzen et al. |
| 5,409,703 A | 4/1995 | McAnalley |
| 5,413,571 A | 5/1995 | Katsaros et al. |
| 5,419,765 A | 5/1995 | Weldon et al. |
| 5,431,639 A | 7/1995 | Shaw |
| 5,437,292 A | 8/1995 | Kipshidze et al. |
| 5,437,631 A | 8/1995 | Janzen |
| 5,441,517 A | 8/1995 | Kensey et al. |
| 5,443,481 A | 8/1995 | Lee |
| 5,464,396 A | 11/1995 | Barta et al. |
| 5,486,195 A | 1/1996 | Myers et al. |
| 5,489,278 A | 2/1996 | Abrahamson |
| 5,514,158 A | 5/1996 | Kanesaka |
| 5,529,577 A | 6/1996 | Hammerslag |
| 5,550,187 A | 8/1996 | Rhee |
| 5,571,181 A | 11/1996 | Li |
| 5,580,923 A | 12/1996 | Yeung |
| 5,591,204 A | 1/1997 | Jansen et al. |
| 5,591,205 A | 1/1997 | Fowler |
| 5,601,602 A | 2/1997 | Fowler |
| 5,626,601 A | 5/1997 | Gershony et al. |
| 5,637,086 A | 6/1997 | Ferguson et al. |
| 5,643,464 A | 7/1997 | Rhee et al. |
| 5,660,849 A | 8/1997 | Polson et al. |
| 5,700,477 A | 12/1997 | Rosenthal |
| 5,716,375 A | 2/1998 | Fowler |
| 5,718,916 A | 2/1998 | Scherr |
| 5,725,498 A | 3/1998 | Janzen et al. |
| 5,725,551 A | 3/1998 | Myers et al. |
| 5,728,122 A | 3/1998 | Leschinsky et al. |
| 5,731,368 A | 3/1998 | Stanley et al. |
| 5,741,223 A | 4/1998 | Janzen et al. |
| 5,744,153 A | 4/1998 | Yewey et al. |
| 5,752,974 A | 5/1998 | Rhee et al. |
| 5,780,044 A | 7/1998 | Yewey et al. |
| 5,782,860 A | 7/1998 | Epstein et al. |
| 5,785,679 A | 7/1998 | Abolfathi et al. |
| 5,795,331 A | 8/1998 | Cragg et al. |
| 5,830,130 A | 11/1998 | Janzen et al. |
| 5,836,970 A | 11/1998 | Pandit |
| 5,843,124 A | 12/1998 | Hammerslag |
| 5,916,236 A | 6/1999 | Muijs Van de Moer et al. |
| 5,922,009 A | 7/1999 | Epstein et al. |
| 5,928,266 A | 7/1999 | Kontos |
| 5,941,847 A | 8/1999 | Huber et al. |
| 5,948,429 A | 9/1999 | Bell |
| 5,948,829 A | 9/1999 | Wallajapet |
| 5,951,583 A | 9/1999 | Jensen et al. |
| 5,951,589 A | 9/1999 | Epstein et al. |
| 5,957,952 A | 9/1999 | Gershony |
| 5,972,375 A | 10/1999 | Truter |
| 5,973,014 A | 10/1999 | Funk |
| 6,017,359 A | 1/2000 | Gershony et al. |
| 6,022,361 A | 2/2000 | Epstein et al. |
| 6,027,471 A | 2/2000 | Fallon et al. |
| 6,045,570 A | 4/2000 | Epstein et al. |
| 6,048,358 A | 4/2000 | Barak |
| 6,051,248 A | 4/2000 | Sawhney et al. |
| 6,056,768 A | 5/2000 | Cates |
| 6,056,769 A | 5/2000 | Epstein et al. |
| 6,063,061 A | 5/2000 | Wallace |
| 6,083,522 A | 7/2000 | Chu |
| 6,152,943 A | 11/2000 | Sawhney |
| 6,162,240 A * | 12/2000 | Cates et al. .................. 606/213 |
| 6,162,241 A | 12/2000 | Coury et al. |
| 6,165,201 A | 12/2000 | Sawhney |
| 6,179,862 B1 | 1/2001 | Sawhney |
| 6,238,412 B1 | 5/2001 | Dubrul et al. |
| 6,271,278 B1 | 8/2001 | Park |
| 6,287,323 B1 | 9/2001 | Hammerslag |
| 6,296,658 B1 | 10/2001 | Gershony |
| 6,299,597 B1 | 10/2001 | Buscemi et al. |
| 6,302,898 B1 | 10/2001 | Edwards et al. |
| 6,350,274 B1 | 2/2002 | Li |
| 6,368,300 B1 | 4/2002 | Fallon et al. |
| 6,371,975 B2 | 4/2002 | Cruise et al. |
| 6,379,373 B1 | 4/2002 | Sawhney |
| 6,458,147 B1 | 10/2002 | Cruise et al. |
| 6,475,177 B1 | 11/2002 | Suzuki |
| 6,514,534 B1 | 2/2003 | Sawhney |
| 6,562,059 B2 | 5/2003 | Edwards et al. |
| 6,566,406 B1 | 5/2003 | Pathak |
| 6,569,185 B2 | 5/2003 | Ungs |
| 6,605,294 B2 * | 8/2003 | Sawhney .................... 424/426 |
| 6,608,117 B1 | 8/2003 | Gvozdic |
| 6,613,070 B2 | 9/2003 | Redmond et al. |
| 6,635,068 B1 | 10/2003 | Dubrul et al. |
| 6,689,148 B2 | 2/2004 | Sawhney |
| 6,699,261 B1 | 3/2004 | Cates et al. |
| 6,703,047 B2 | 3/2004 | Sawhney |
| 6,774,151 B2 | 8/2004 | Malmgren |
| 6,818,008 B1 | 11/2004 | Cates |
| 6,818,018 B1 | 11/2004 | Sawhney |
| 6,863,924 B2 | 3/2005 | Ranganathan |
| 6,887,974 B2 | 5/2005 | Pathak |
| 6,960,617 B2 | 11/2005 | Omidian |
| 2001/0031948 A1 | 10/2001 | Cruise et al. |
| 2001/0046518 A1 | 11/2001 | Sawhney |
| 2001/0047187 A1 | 11/2001 | Milo et al. |
| 2001/0051813 A1 | 12/2001 | Hnojewyj |
| 2002/0015724 A1 | 2/2002 | Yang et al. |
| 2002/0062104 A1 | 5/2002 | Ashby et al. |
| 2002/0072767 A1 | 6/2002 | Zhu |
| 2002/0106409 A1 | 8/2002 | Sawhney et al. |
| 2002/0111392 A1 | 8/2002 | Cruise |
| 2002/0111651 A1 | 8/2002 | Ungs |
| 2002/0188319 A1 | 12/2002 | Morris et al. |
| 2003/0008831 A1 | 1/2003 | Yang et al. |
| 2003/0012734 A1 | 1/2003 | Pathak |
| 2003/0051735 A1 | 3/2003 | Pavcnik et al. |
| 2003/0088269 A1 | 5/2003 | Ashby |
| 2003/0088271 A1 | 5/2003 | Cragg et al. |
| 2003/0135234 A1 | 7/2003 | Fisher et al. |
| 2003/0135235 A1 | 7/2003 | Fisher et al. |
| 2003/0135236 A1 | 7/2003 | Fisher et al. |
| 2003/0139770 A1 | 7/2003 | Fisher et al. |
| 2003/0139771 A1 | 7/2003 | Fisher et al. |
| 2003/0139772 A1 | 7/2003 | Fisher et al. |
| 2003/0139773 A1 | 7/2003 | Fisher et al. |
| 2003/0233120 A1 | 12/2003 | Akerfeldt |
| 2004/0122350 A1 | 6/2004 | Zhong et al. |
| 2004/0147016 A1 | 7/2004 | Rowley |

| | | | |
|---|---|---|---|
| 2004/0249342 A1 | 12/2004 | Khosravi | |

FOREIGN PATENT DOCUMENTS

| | | |
|---|---|---|
| EP | 0 482 350 B1 | 4/1992 |
| WO | WO 92/22252 | 12/1992 |
| WO | 0014155 | 3/2000 |
| WO | 0019912 | 4/2001 |
| WO | 03094749 | 11/2003 |

OTHER PUBLICATIONS

PCT Written Opinion for PCT/USUS2005/039692, Applicant: Accessclosure, Inc., Form PCT/ISA/237, dated Mar. 21, 2006 (6 pages).

\* cited by examiner

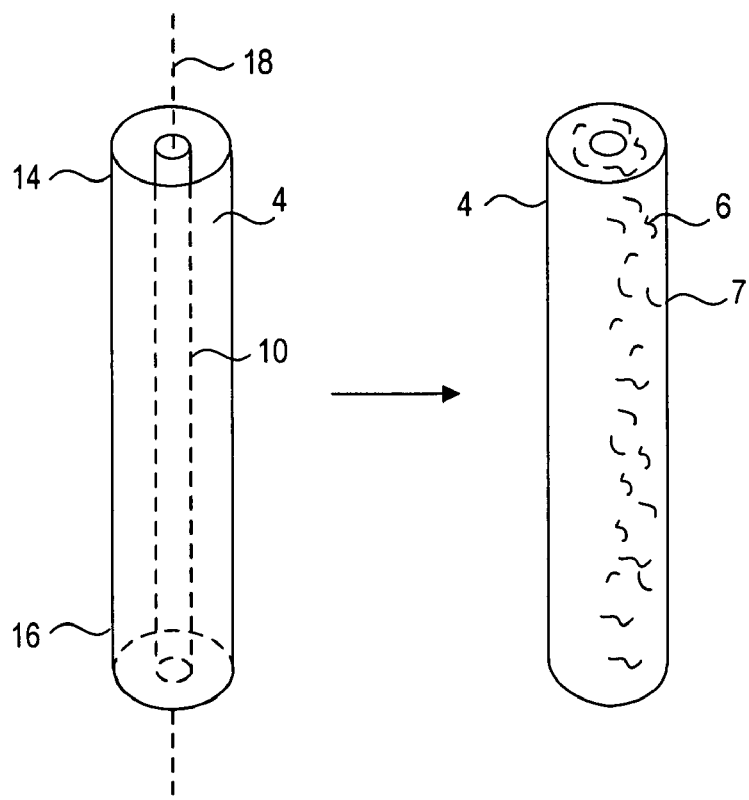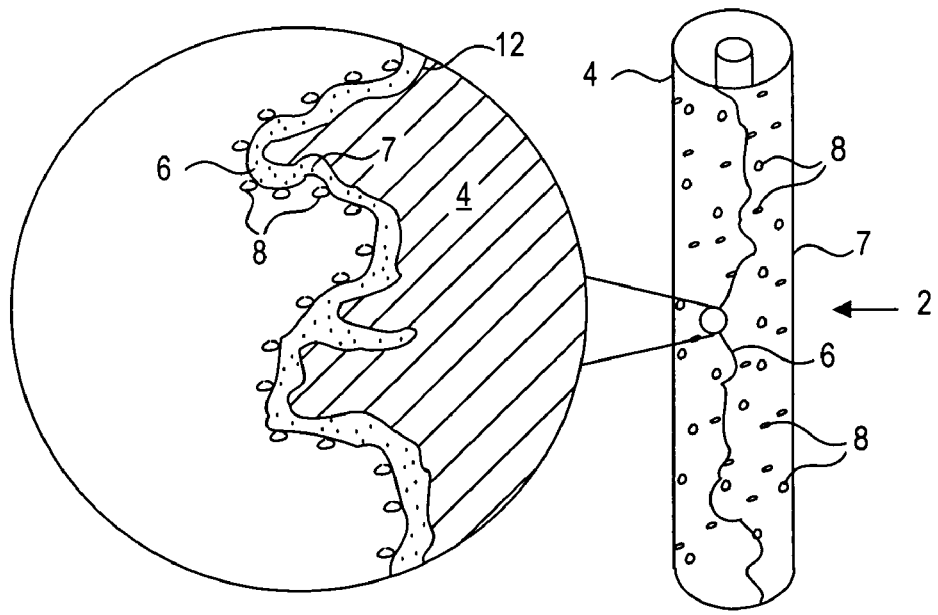
Fig. 1A  Fig. 1B
Fig. 1D  Fig. 1C

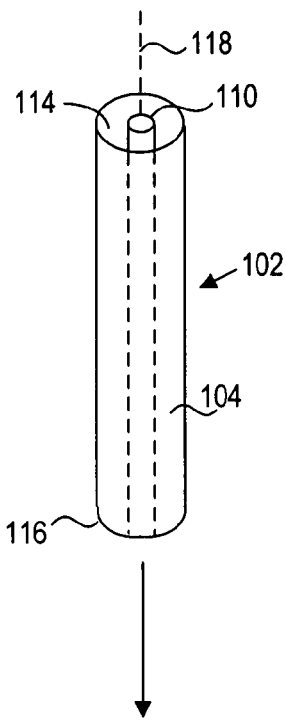
Fig. 6A
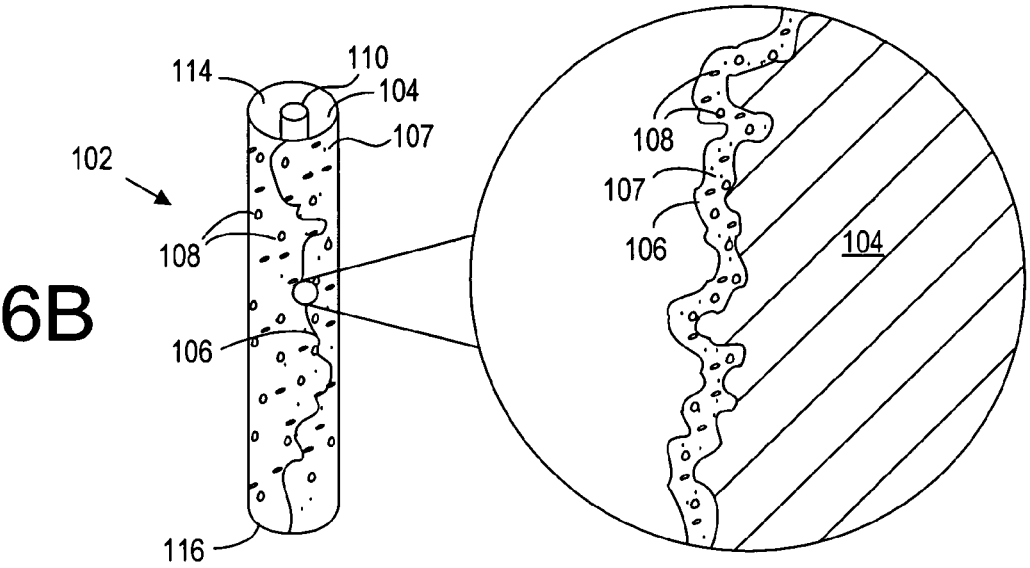
Fig. 6B
Fig. 6C

APPARATUS AND METHODS FOR SEALING A VASCULAR PUNCTURE

FIELD OF THE INVENTION

The present invention relates generally to apparatus and methods for sealing punctures in a body, and more particularly, to apparatus and methods for sealing a vascular puncture extending through tissue into a blood vessel, and to apparatus and methods for delivering a plug into a percutaneous puncture extending from a patient's skin to a blood vessel or other body lumen to seal the puncture.

BACKGROUND

Apparatus and methods are known for accessing a patient's vasculature percutaneously, e.g., to perform a procedure within the vasculature, and for sealing the puncture that results after completing the procedure. For example, a hollow needle may be inserted through a patient's skin and overlying tissue into a blood vessel. A guide wire may be passed through the needle lumen into the blood vessel, whereupon the needle may be removed. An introducer sheath may then be advanced over the guide wire into the vessel, e.g., in conjunction with or subsequent to one or more dilators.

A catheter or other device may be advanced through the introducer sheath and over the guide wire into a position for performing a medical procedure. Thus, the introducer sheath may facilitate accessing and/or introducing various devices into the vessel, while minimizing trauma to the vessel wall and/or minimizing blood loss. Upon completing the procedure, the device(s) and introducer sheath may be removed, leaving a puncture extending between the skin and the vessel wall.

To seal the puncture, external pressure may be applied to the overlying tissue, e.g., manually and/or using sandbags, until hemostasis occurs. This procedure, however, may be time consuming and expensive, requiring as much as an hour of a medical professional's time. It is also uncomfortable for the patient, and may require the patient to remain immobilized in the operating room, catheter lab, or holding area. In addition, a risk of hematoma exists from bleeding before hemostasis occurs.

Various apparatus and methods have been suggested for sealing a percutaneous puncture instead of using external pressure. For example, U.S. Pat. No. 5,108,421 to Fowler discloses a plug that may be delivered into a puncture through tissue. The plug is a cylindrical rod-shaped member which is constructed of a porous, bioabsorbable and expandable hemostatic collagen sponge or a polymerized polylactic acid or polyglycolic acid. In one embodiment, a catheter is inserted through the puncture into the blood vessel. A balloon on the catheter is expanded and retracted until the balloon is disposed adjacent the puncture at the wall of the vessel. The plug may be advanced into the puncture until the plug contacts the balloon. Once the plug is positioned within the puncture, the balloon may be deflated and withdrawn, leaving the plug within the puncture to expand and seal the puncture and/or to promote hemostasis.

Alternatively, U.S. Pat. Nos. 5,192,302 and 5,222,974 issued to Kensey et al. describe a bioabsorbable collagen plug that may be delivered through an introducer sheath into a puncture site. The disclosed plug, however, may be difficult to position properly with respect to the vessel, which may be significant since it is generally undesirable to expose the collagen material within the bloodstream where it may float downstream and cause an embolism.

U.S. Pat. No. 6,605,295 describes rods, plugs, crushed or irregularly shaped pieces of substantially dehydrated hydrogel that may be introduced into a lumen or void in a patient's body to seal or plug a biopsy needle track, reinforce weak tissue, or deliver a therapeutic compound. In one embodiment, a plug of dehydrated hydrogel may be deployed into the site of an arteriotomy and allowed to hydrate in the presence of the tissue fluids and blood, to fill the track of the catheter sheath and prevent further bleeding. By swelling to equilibrium hydration, the plug may lock itself firmly in place and thus reduce the risk of formation of a large hematoma at the site of the puncture.

U.S. Pat. No. 6,703,047 discloses dehydrated hydrogel precursor-based, tissue adherent compositions. The hydrogels may be used, for example, for sealing fluid leaks from tissue, as adherent drug delivery depots, and as means for augmenting and/or supporting tissue. The hydrogels may be administered directly to an open wound site or may be dispensed, e.g., using a non-adhesive backing material, an absorbable backing material, a syringe applicator, a powder atomization or aerosolization system, or a needle-less injector.

SUMMARY OF THE INVENTION

The present invention is directed to apparatus and methods for sealing a puncture in a body, and, more particularly, to apparatus and methods for providing temporary or permanent hemostasis within a vascular puncture extending into a blood vessel, and/or to apparatus and methods for delivering a sealing plug into a percutaneous puncture extending from a patient's skin to a blood vessel or other body lumen.

In accordance with one embodiment, a device is provided for sealing a puncture extending through tissue including a carrier having a predetermined shape, e.g., a disk, cylinder, or other plug. A first hydrogel precursor is disposed on the carrier. A second hydrogel precursor is also disposed on the carrier. The first and second hydrogel precursors are disposed on the carrier in an unreactive state before exposure to an aqueous physiological environment.

In accordance with another embodiment, an apparatus is provided for sealing a puncture extending through tissue that includes a tubular member and a plug carried by the tubular member. The plug may include first and second hydrogel precursors disposed thereon, the first and second hydrogel precursors being in an unreactive state prior to exposure to an aqueous physiological environment in the tissue. The device may include a pusher member for deploying the plug from the tubular member.

In one embodiment, the plug may include a lumen extending therethrough. The device may also include a pusher member and a positioning member adapted to slide and/or pass through the tubular member. The positioning member may include an elongate member and an expandable element on one end, e.g., an expandable mesh, balloon, expandable frame, and the like, on a guidewire. In an alternative embodiment, the positioning member may include a bioabsorbable foot plate or other element on one end, e.g., for providing tactile feedback to the user during a sealing procedure and/or sealing the puncture.

In accordance with yet another embodiment, a method is provided for sealing a puncture extending through tissue and/or communicating with a body lumen. The method may include delivering a plug into a puncture, the plug including first and second hydrogel precursors disposed on a core, and a pH activating agent, the first and second hydrogel precursors being in an unreactive state before being exposed to an aqueous physiological environment in the tissue.

In accordance with still another embodiment, a method is provided for making a device for sealing a puncture extending through tissue. A porous carrier and/or other core may be provided, e.g. in the shape of a plug, and first and second precursors may be applied to the core. In one embodiment, the first and second precursors may remain in an unreactive state until exposed to an aqueous physiological environment in the tissue. Once exposed to an aqueous physiological environment, e.g., when exposed to fluid within a puncture, the first and second precursors may react with one another to create a hydrogel, an adhesive, and/or other composition surrounding the core that may enhance attachment of the carrier to tissue surrounding the puncture and/or hemostasis within the puncture.

In accordance with still another embodiment, a device is provided for sealing a puncture extending through tissue including a lyophilized hydrogel, e.g., polyethylene glycol (PEG), or other polymer carrier. The polymer used in the carrier includes hydrolytically degradable chemical groups, thereby permitting in vivo degradation.

In one embodiment, lyophilized PEG carrier is pre-formed into a desired shape or geometry before the lyophilization process. In another embodiment, the lyophilized PEG carrier is formed into the desired shape or geometry after the lyophilization process. For example, "raw" lyophilized PEG carrier material may be shaped or otherwise modified by processes such as die cutting, rolling, flattening, compression molding, and the like.

In accordance with another embodiment, any of the devices described above may include an adherent "sticky" coating or layer disposed on an exposed surface of the polymer carrier. The adherent coating may be formed from a mixture of un-cross-linked PEG polymers and a pH adjusting agent such as, sodium borate crystals. In an exemplary process, the adherent coating mixture may be heated to melt the polymer components and then applied to the lyophilized PEG carrier.

In accordance with another embodiment, an apparatus is provided for sealing a puncture extending through tissue that includes a cartridge and a plug device formed from a lyophilized PEG carrier. The plug may include first and second PEG polymers disposed thereon, the first and second PEG polymers being in an unreactive state prior to exposure to an aqueous physiological environment in the tissue. The apparatus may include a pusher member for deploying the plug from the cartridge, a positioning member, and/or an occlusion member.

In accordance with yet another embodiment, a method is provided for sealing a puncture extending through tissue and/or communicating with a body lumen. The method may include delivering a plug formed from a lyophilized polymer, such as PEG or other hydrogel, into a puncture, and exposing the plug to bodily fluids, thereby causing substantial expansion of the lyophilized material to enhance hemostasis within the puncture. In one form, the plug may include an adherent layer formed from first and second PEG polymers carried in an unreactive state and/or a pH activating agent, similar to other embodiments described herein.

Other aspects and features of the present invention will become apparent from consideration of the following description taken in conjunction with the accompanying drawings.

BRIEF DESCRIPTION OF THE DRAWINGS

FIG. 1A is a perspective view of a porous carrier in the shape of a plug.

FIG. 1B is a perspective view of the porous carrier of FIG. 1A having first and second hydrogel precursors disposed thereon.

FIG. 1C is a perspective view of the porous carrier of FIG. 1B having a pH activating agent disposed thereon.

FIG. 1D is a magnified cross-sectional view of the porous carrier shown in FIG. 1C, including the first and second hydrogel precursors and the pH activating agent.

FIG. 6A is a perspective view of a lyophilized carrier in the shape of a plug.

FIG. 6B is a perspective view of the lyophilized carrier of FIG. 6A having an adherent layer disposed thereon to provide a plug device for sealing a puncture through tissue.

FIG. 6C is a magnified cross-sectional view of the plug device of FIG. 6B, showing first and second polymers and pH activating agent carried on the plug device.

DETAILED DESCRIPTION OF THE PREFERRED EMBODIMENTS

Figure 2:
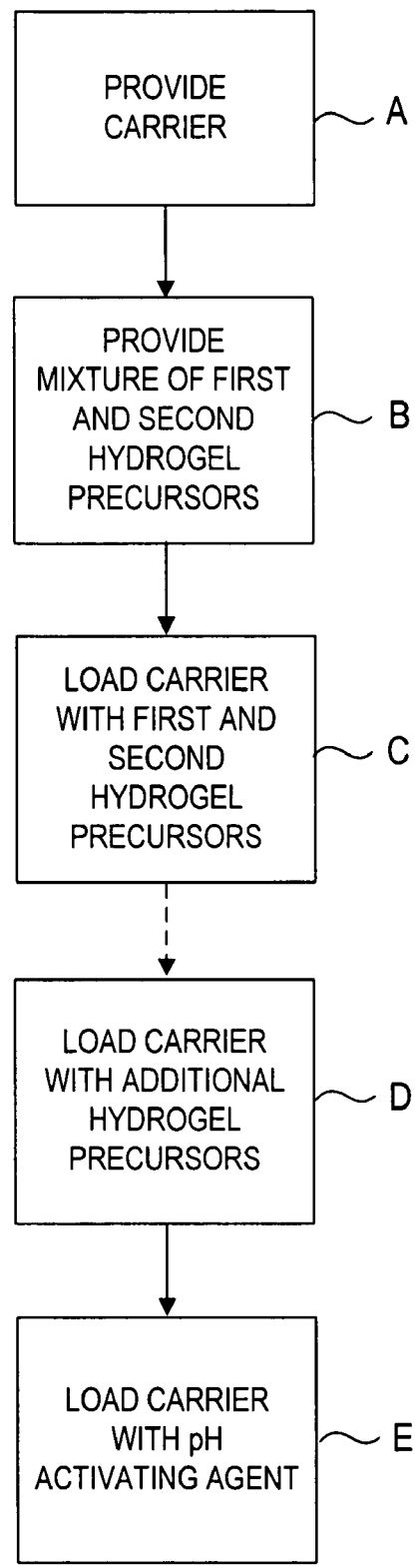
FIG. 2 is a flowchart showing a method for loading two or more hydrogel precursors on a porous carrier.

Turning to the drawings, FIGS. 1A-1D illustrate a device 2 for sealing a puncture extending through tissue (not shown). Generally, the device 2 includes a carrier or core 4, e.g., in the shape of a plug, having disposed thereon a first hydrogel precursor 6 and a second hydrogel precursor 7. The first and second hydrogel precursors 6, 7 are disposed on the carrier 4 in an unreactive state. The first and second hydrogel precursors 6, 7 may remain in the unreactive state, e.g., before or until exposure to an aqueous physiological environment. An aqueous physiological environment may exist, for example, inside a puncture track extending through tissue.

Blood or other bodily fluids that contact the precursor-laden carrier 4 may initiate a hydrogel forming reaction between the two precursors 6, 7. The reaction of the hydrogel precursors may form a cross-linked adhesive or tacky coating that may aid in retaining the plug device 2 within a puncture after deployment and/or in facilitating hemostasis within the puncture. Optionally, as described below, an activating agent, e.g., a pH adjusting material 8, may also be disposed on the carrier 4 to initiate, accelerate, or otherwise enhance the reaction of the precursors 6, 7.

FIG. 1A illustrates a carrier 4 in the shape of a circular cylindrical plug. It will be appreciated that the carrier 4 may have other cross-sections or shapes, such as elliptical, triangular, square, conical, disk, polygonic shapes, etc. The carrier 4 may be formed from a biocompatible and/or bioabsorbable material, for example, a porous, bioabsorbable foam or other solid material. In one embodiment, the carrier 4 may be formed from a biocompatible and/or bioabsorbable hydrogel, e.g., polyethylene glycol ("PEG"), or other synthetic material. In addition or alternatively, the carrier 4 may include pro-thrombotic material, e.g., including one or more biological pro-thrombotics, such as collagen, fibrin, carboxymethylcellulose, oxidized cellulose, alginates, gelatin, or other protein-based material, and/or synthetic materials, such as polyglycolic acids (PGA's), polyactides (PLA's), polyvinyl alcohol, and the like. The material of the carrier 4 may be at least partially absorbed by the body over time, e.g., over a period of days, weeks, or months. Optionally, the carrier 4 may include therapeutic and/or pharmaceutical agents, e.g., to promote healing, prevent infection and/or other adverse medical events, and the like. Such agents may be embedded in the carrier material and/or applied as one or more coatings or layers. In addition, the material of the carrier 4 may have a substantially uniform composition or the composition may be varied, e.g., along its length and/or within underlying layers within the carrier 4.

In the embodiment shown, the carrier 4 includes a lumen 10 extending between proximal and distal ends 14, 16, thereby defining a longitudinal axis 18. The lumen 10 may be created when the carrier 4 is formed, e.g., if the carrier 4 is rolled from one or more sheets or layers of material or formed by molding. Alternatively, the lumen 10 may formed by boring into or otherwise removing material from an already formed solid carrier 4. The lumen 10 is dimensioned such that a guide wire or other elongate member, such as a portion of a positioning member 40 (described in more detail below) may slide or otherwise pass through the carrier 4, e.g., while delivering the plug device 2.

FIG. 1B illustrates the carrier 4 loaded with first and second hydrogel precursors 6, 7 thereon. In one embodiment, the first and second hydrogel precursors 6, 7 are loaded onto the carrier 4 by wicking a mixture of the liquid hydrogel precursors 6, 7 onto the carrier 4. Depending on the material used, the hydrogel precursors 6, 7 may initially be a solid dehydrated material, e.g., a powder, that may be heated above its melting point to form a liquid suitable for wicking. For example, the first and second hydrogel precursors 6, 7 may be sufficiently mixed before being loaded onto the carrier 4.

Alternatively, the first and second precursor materials 6, 7 may be provided in a liquid form into which the carrier 4 may be dipped, that may be poured onto the carrier 4, and/or otherwise applied to the carrier 4 together or successively. For example, the first and second precursors may be dissolved in a solvent that may then be applied to the carrier 4. In either case, once the first and second hydrogel precursors 6, 7 are loaded onto the carrier 4, the first and second hydrogel precursors 6, 7 may be in a solid or semi-solid state.

The first hydrogel precursor 6 may include any number of hydrogel precursor materials, such as those disclosed in U.S. Pat. Nos. 6,152,943, 6,165,201, 6,179,862, 6,514,534, 6,379,373, 6,703,047, and in co-pending application Ser. Nos. 10/010,715 filed Nov. 9, 2001, Ser. No. 10/068,807 filed Feb. 5, 2002, and Ser. No. 10/454,362, filed Jun. 4, 2003. The disclosures of these references and any others cited therein are expressly incorporated by reference herein. For example, in one embodiment, the first hydrogel precursor 6 may include a four arm, 10 kDalton PEG with reactive ester end groups or an eight arm, 20 kDalton PEG amine. Alternatively, the first hydrogel precursor 6 may include a bioabsorbable star polymer having a complementary cross-linking species such as, for example, an amino acid with reactive end groups, e.g., lysine, dilysine, trilysine, etc.

The second hydrogel precursor 7 may include any number of hydrogel precursor materials, e.g., a material reactive with the first precursor material 6 once exposed within a hydrous or aqueous environment, such as those materials disclosed above and in the references incorporated by reference above. For example, the second precursor 7 may be the other of an eight arm, 20 kDalton PEG amine or a four arm, 10 kDalton PEG ester. Alternatively, the second precursor 7 may be the complementary cross-linking species of a bioabsorbable star polymer, such as an amino acid with reactive end groups, e.g., lysine, dilysine, trilysine, etc.

Referring to FIG. 1C, a pH activating agent 8 is also loaded onto the carrier 4. The pH activating agent 8 may create a localized change in pH after exposure to a hydrous or aqueous environment, e.g., to initiate or accelerate the hydrogel-forming reaction. In an exemplary embodiment, the pH activating agent 8 includes solid borate crystals, such as $Na_2B_4O_7 \cdot 10H_2O$, although different salt-based or other materials that alter the localized pH value may be employed. Alternatively, other pH altering agents may be used, such as sodium borate, sodium bicarbonate, and the like. In one embodiment, the pH activating agent 8 is loaded onto the carrier 4 by physically contacting solid borate crystals, powder, or other particles onto the precursor-laden (first and second hydrogel precursors 6, 7) carrier 4. For example, the carrier 4 may simply be rolled over a pH activating agent 8 with sufficient force to embed the pH activating agent 8 into the exterior surface 12 of the carrier 4. Alternatively, the pH activating agent 8 may be adhered to the exterior surface 12 of the carrier 4, e.g., by pressing particles of the pH activating agent 8 into the exterior surface 12, by using an adhesive (e.g., that is substantially inert or unreactive with the first or second precursors 6, 7), and the like.

FIG. 1D illustrates a magnified cross-sectional view of the exterior surface 12 of the precursor-laden carrier 4 of FIG. 1D. As shown, a layer of the mixed first and second hydrogel precursors 6, 7 substantially coats the exterior surface 12 of the carrier 4 in a relatively thin film or coating. Because the first and second hydrogel precursors 6, 7 are preferably in liquid form during the wicking process, the first and second hydrogel precursors 6, 7 may penetrate into the exterior surface 12 of the porous carrier 4, e.g., into pores or other recesses to substantially coat all or a significant portion of the carrier 4.

FIG. 1D further shows the pH activating agent 8 loaded onto the carrier 4. In FIG. 1D, the pH activating agent 8 is in the form of a solid (e.g., borate crystals) with individual particles populated on top of the layer of first and second hydrogel precursors 6, 7. It should be understood, however, that the pH activating agent 8 may be loaded onto the carrier 4 in a melted or other liquid form that remains unreactive with the first and second hydrogel precursors 6, 7 in which case the pH activating agent 8 may form a film, coating, or layer much like that shown of the first and second hydrogel precursors 6, 7 in FIG. 1D.

Turning to FIG. 2, a flowchart shows an exemplary method for making a sealing device, such as plug device 2 described above. First, a carrier 4 is provided (step A), e.g., by forming a plug or other body from a porous, pro-thrombotic, and/or biocompatible material. As described above, the carrier 4 may be formed by rolling material into a desired shape, by molding, by cutting individual devices from a larger mass of material, machining, grinding, and the like. Next, a mixture of first and second hydrogel precursors 6, 7 is provided (step B) in a predetermined ratio, e.g., an equimolar ratio. The carrier 4 is then loaded with first and second precursors 6, 7 (step C), which, as described above, may be hydrogel precursors in liquid form. Optionally, as shown in FIG. 2, the carrier 4 may be loaded with one or more additional layers of hydrogel precursor material (step D). Depending on the hydrogel employed in the plug device 2, there may be multiple hydrogel (e.g., more than two) precursors needed to initiate the hydrogel reaction. In further options, one or more therapeutic and/or pharmaceutical agents may be applied to the carrier 4, e.g., before or after coating the carrier 4 with the first and second precursors 6, 7.

Finally, an optional pH activating agent 8 may be loaded on the carrier 4 (step E). In one embodiment, the pH activating agent 8 is in crystalline or other particle form that may be physically adhered to the carrier 4, e.g., on top of the first and second precursors 6, 7.

Figure 3:
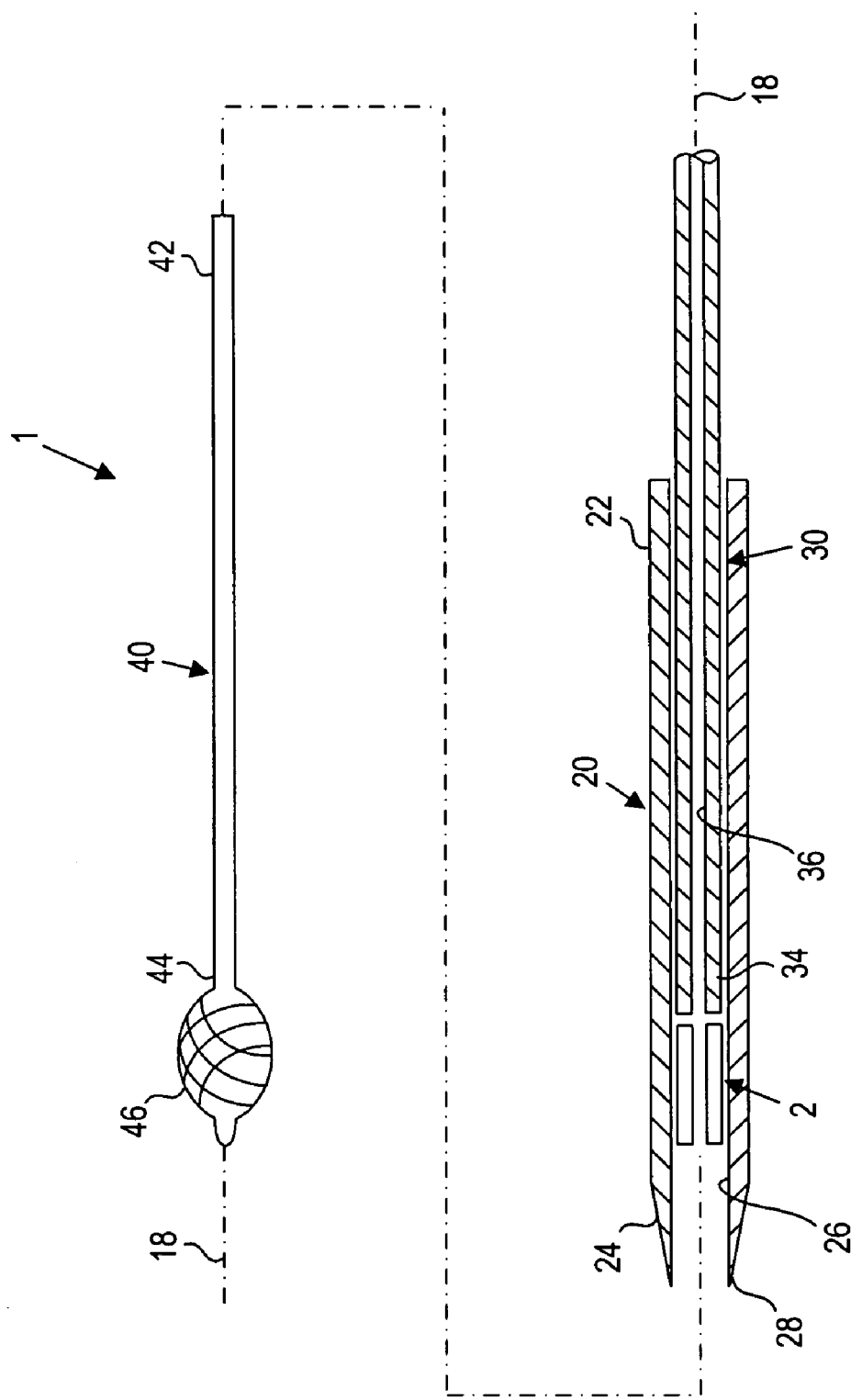
FIG. 3 is an exploded side view of an apparatus for delivering a plug device into a puncture through tissue.

Turning to FIG. 3, an apparatus 1 is shown for sealing a puncture through tissue. Generally, the apparatus 1 may include a delivery sheath or other tubular member 20 and a plug device 2, such as those described elsewhere herein. In addition, the apparatus 1 may include a plunger or other pusher member 30, and/or a positioning member 40.

The delivery sheath 20 may be a substantially rigid, semi-rigid, and/or flexible tubular body, including a proximal end 22, a distal end 24 having a size and shape for insertion into the puncture 90, and a lumen 26 extending therebetween. The distal end 24 may be tapered and/or may include a substantially atraumatic tip 28 to facilitate advancement through a puncture. The delivery sheath 20 may include a handle (not shown), and/or one or more seals, e.g., a hemostatic seal (also not shown), on the proximal end 22. The plug device 2 may be disposed within the lumen 26 proximate to the distal end 24. The lumen 26 may be sized such that the plug device 2 is slidable therein, e.g., able to traverse distally from the delivery sheath 20 during delivery, as described further below.

The pusher member 30 may be an elongate member, e.g., a plunger, catheter, and the like, including a proximal end (not shown), and a distal end 34 having a size for slidable insertion into the lumen 26 of the delivery sheath 20. The distal end 34 of the pusher member 30 may be substantially blunt to facilitate contacting, pushing, and/or "cinching" the plug device 2 within the delivery sheath 20 and/or puncture, as described further below. The pusher member 30 may be substantially rigid, semi-rigid, and/or substantially flexible, having sufficient column strength to allow movement of the delivery sheath 20 relative to the plug device 2 without buckling the pusher member 30. The pusher member 30 may also include a lumen 36 extending between the proximal end and the distal end 34, e.g., to accommodate the positioning member 40 and/or a guidewire (not shown).

Figure 4A:
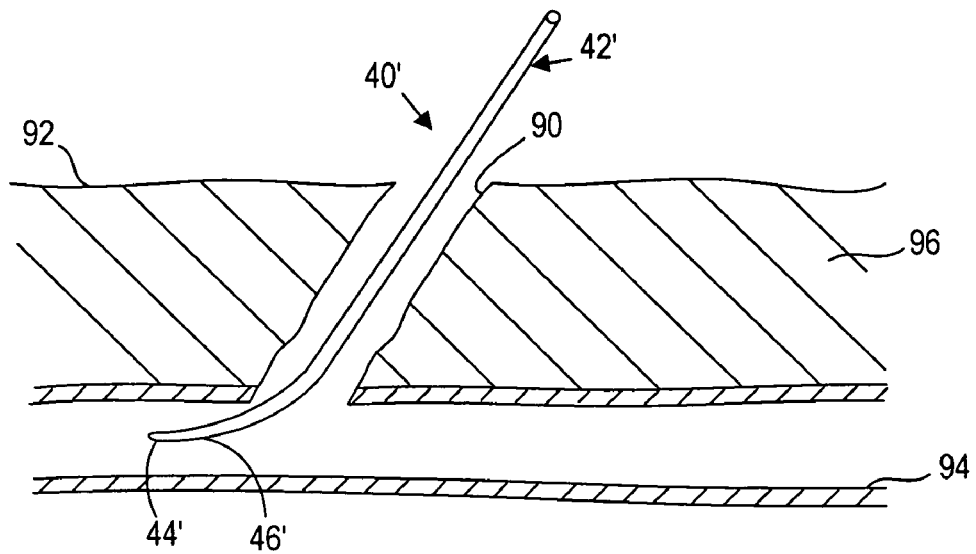
FIGS. 4A-4F are cross-sectional views of a patient's body, showing a method for sealing a puncture extending from the patient's skin through intervening tissue to a body lumen.
Figure 4B:
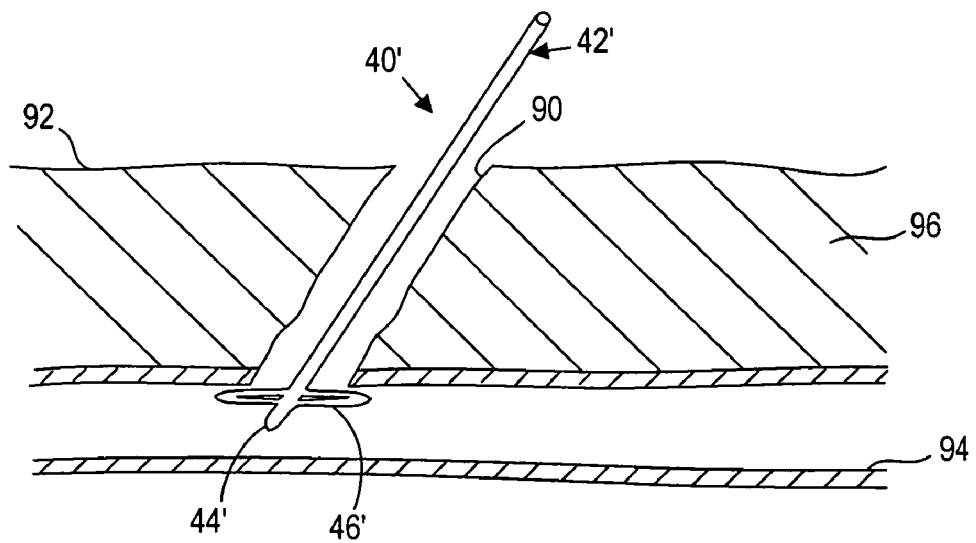
Figure 4C:
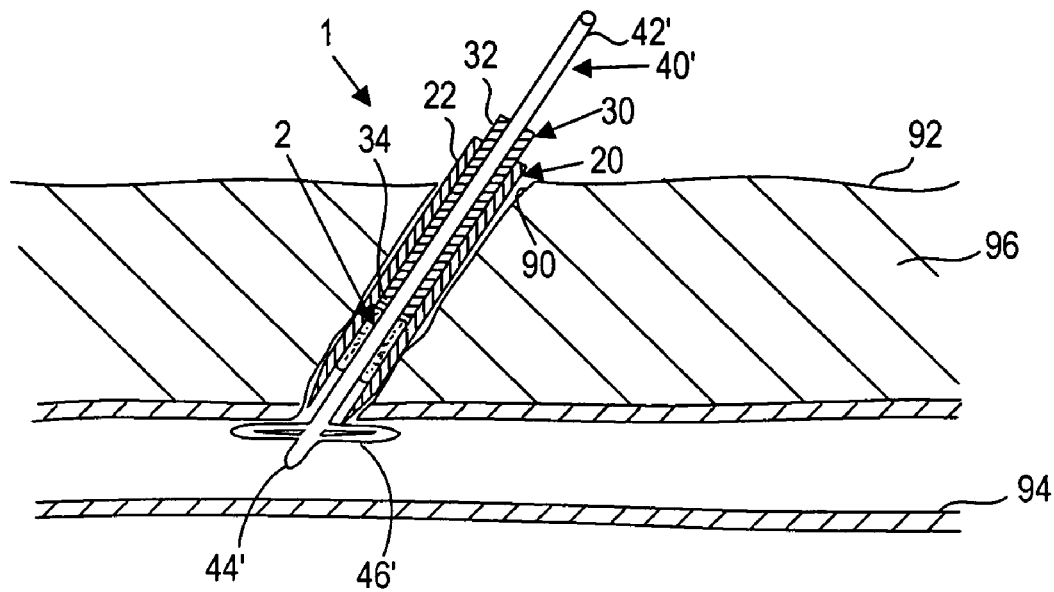

In the embodiment shown in FIG. 3, the positioning member 40, e.g., a guidewire, and/or other solid or hollow elongate body, may include a proximal end 42, a distal end 44, and a positioning element 46 on the distal end 44. The positioning element 46 may be an expandable element, such as a wire mesh structure, as shown in FIG. 3, an expandable frame 46', as shown in FIGS. 4A-4C, and/or a balloon (not shown). Optionally, the positioning element 46 or 46' may include a skin or other covering (not shown) on at least a proximal portion thereof, thereby making the positioning element 46 or 46' substantially nonporous.

The positioning element 46 or 46' may be biased to an enlarged condition, such as that shown in FIGS. 3 and 4A-4C, but may be compressed to a contracted condition, e.g., by an overlying sleeve or other constraint (not shown). The constraint may be removed to expose the expandable element, allowing the expandable element to automatically expand to the enlarged condition. Alternatively, the expandable element may be selectively expandable, e.g., using a pullwire, source of inflation media (e.g., coupled to a lumen (not shown) extending through the positioning member 40 to an inflatable positioning element, not shown), or other actuator (also not shown) operable from the proximal end of the position member 40. Additional information on expandable structures that may be incorporated into positioning member 40 may be found in U.S. Pat. Nos. 6,238,412 and 6,635,068, in application Ser. No. 10/143,514, published as Publication No. US 2003/0078616 A1, and Ser. No. 10/975,205, filed Oct. 27, 2004 and entitled "Apparatus and Methods for Delivering Sealing Materials During a Percutaneous Procedure to Facilitate Hemostasis". The entire disclosures of these references are expressly incorporated herein by reference.

Turning to FIGS. 4A-4F, an exemplary method is shown for sealing a puncture 90 using an apparatus 1. Generally, the puncture 90 extends from a patient's skin 92 through intervening tissue 96, e.g., to a body lumen 94. In an exemplary embodiment, the puncture 90 may be a percutaneous puncture communicating with a blood vessel 94, such as a femoral artery, carotid artery, and the like.

In an exemplary method, the puncture 90 may be created using known procedures, e.g., using a needle, guidewire, one or more dilators, and the like (not shown). An introducer sheath (also not shown) may be advanced through the puncture 90 into the vessel 94, e.g., to provide access into the vessel 90 for one or more instruments, and/or allow one or more diagnostic and/or interventional procedures to be performed via the vessel 90, as is known in the art. Upon completing the procedure(s) via the vessel 94, any instruments and/or the introducer sheath (not shown) may be removed from the puncture 90.

Turning to FIG. 4A, with the positioning element 46 collapsed, the positioning member 40 may be advanced through the puncture 90 until the positioning element 46 is disposed within the vessel 94, whereupon the positioning element 46 may be expanded to the enlarged condition shown in FIG. 4B. In one embodiment, the positioning member 40 may be advanced through a previously placed introducer sheath (not shown), e.g., before the introducer sheath is removed from the puncture 90. Alternatively, the positioning member 40 may be advanced directly through the puncture 90 after the introducer sheath is removed.

The positioning element 46 may be maintained in the contracted condition (shown in FIG. 4A) as it is advanced through the puncture 90, e.g., by an overlying sheath or other constraint (not shown). Once the positioning element 46 is disposed within the vessel 94, the constraint may be removed, allowing the positioning element 46 to expand automatically to the enlarged condition (shown in FIG. 4B). Alternatively, the positioning element 46 may be expanded to the enlarged condition via an actuator (not shown) on the proximal end 42 of the positioning member 40.

As shown in FIG. 4B, once the positioning element 46 is expanded, the positioning member 40 may be partially withdrawn from the puncture 90 until the positioning element 46 contacts the wall of the vessel 94, as shown in FIG. 4B. If the positioning element 46 is substantially nonporous, the positioning element 46 may substantially seal the puncture 90 from the vessel 94.

Turning to FIG. 4C, the apparatus 1 may be introduced into the puncture 90, e.g., before or after the positioning element 46 is directed into contact with the wall of the vessel 94. For example, the proximal end 42 of the positioning member 40 may be backloaded into the distal end 24 of the delivery sheath 20, e.g., through the lumens 26, 10, 36 of the delivery sheath 20, plug device 2, and pusher member 30, respectively. The delivery sheath 20 may then be advanced over the positioning member 40, e.g., until the distal end 24 is disposed adjacent the vessel 94.

If the positioning element 46 has not yet been retracted, the proximal end 42 of the positioning member 40 may be pulled to draw the positioning element 46 against the distal end 24 of the delivery sheath 20 (providing a tactile feedback). The positioning member 40 may then be pulled further until the positioning element 46 contacts the wall of the vessel 94 (providing another tactile feedback), thereby partially in retracting the delivery sheath 20 back into the puncture 90.

Alternatively, if the positioning element 46 is already against the wall of the vessel 94, the delivery sheath 20 may be advanced until the distal end 24 contacts the positioning element 46, thereby providing a tactile indication that the distal end 24, and consequently the plug device 2, are disposed adjacent the vessel 94. If the positioning element 46 substantially seals the puncture 90 from the vessel 94, this may prevent or minimize blood within the vessel 94 from entering the puncture 90, where it may seep into the lumen 26 of the delivery sheath 20 and contact the plug device 2. This may be desirable to reduce any premature reaction between the first and second precursors on the plug device 2.

Figure 5A:
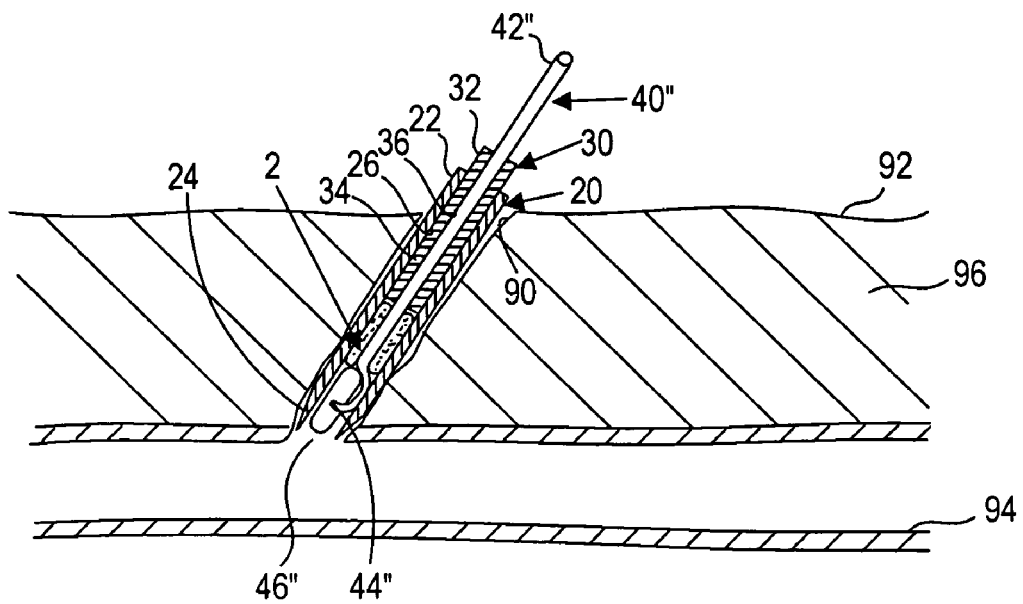
FIGS. 5A and 5B are cross-sectional views of a patient's body, showing another apparatus and method for sealing a puncture extending from a patient's skin through intervening tissue to a body lumen.
Figure 5B:
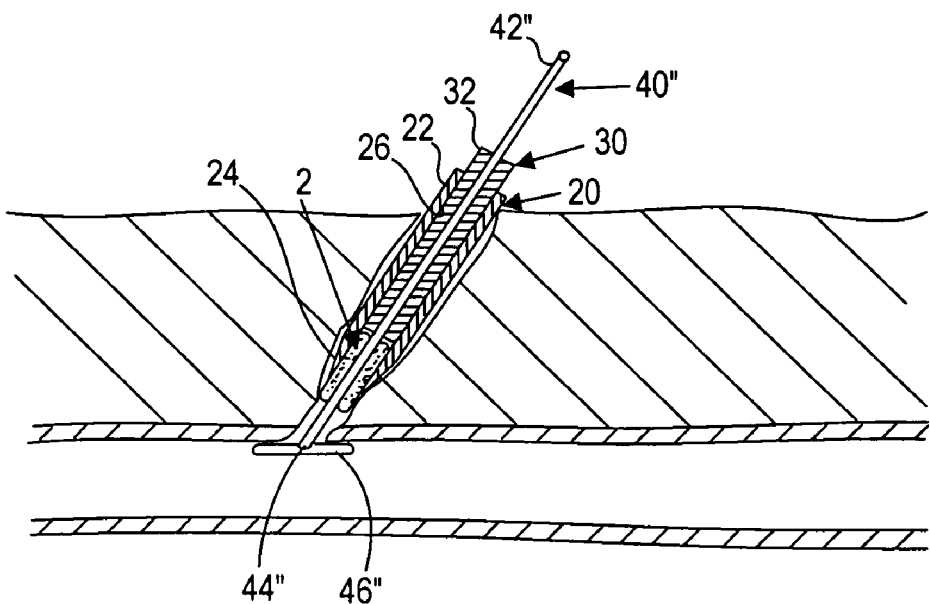

Alternatively, the positioning member 40 may be carried initially within the delivery sheath 20. For example, as shown in FIGS. 5A and 5B, the positioning member 40" may include a foot plate 46" on a distal end 44" thereof that may be stored within the lumen 26 of the delivery sheath 20 distal to the plug device 2. As shown in FIG. 5A, the delivery sheath 20 may be advanced into the puncture 90, e.g., directly or through the introducer sheath (before its removal) with the foot plate 46" therein. Once the distal end 24 of the delivery sheath 20 is disposed within the vessel 94, the positioning member 40" may be advanced to expose the foot plate 46" within the vessel 94. The foot plate 46" may change orientation once exposed and/or may expand radially. Thereafter, the positioning member 40" may be partially retracted to direct the foot plate 46" into contact with the wall of the vessel 94, preventing the positioning member 40" from being withdrawn further. If the foot plate 46" has sufficient width, it may substantially seal the puncture 90 from the vessel 94.

In yet another alternative, before introducing the positioning member 40, the delivery sheath 20 may be advanced into the puncture 90, e.g., over a guidewire (not shown); which may remain after removing the introducer sheath, through the introducer sheath (before its removal), or directly through the puncture 90. After removing any guidewire, the positioning member 40 may be advanced into the proximal end 22 of the delivery sheath 20 and through the lumen 10 of the plug device 2, e.g., with the positioning element 46 in the contracted condition. The distal end 24 of the positioning member 40 may be advanced distally until the positioning element 46 is disposed within the vessel 94. Once within the vessel 94, the positioning element 46 may be expanded and directed into contact with the wall of the vessel 94, similar to the methods described above.

Figure 4D:
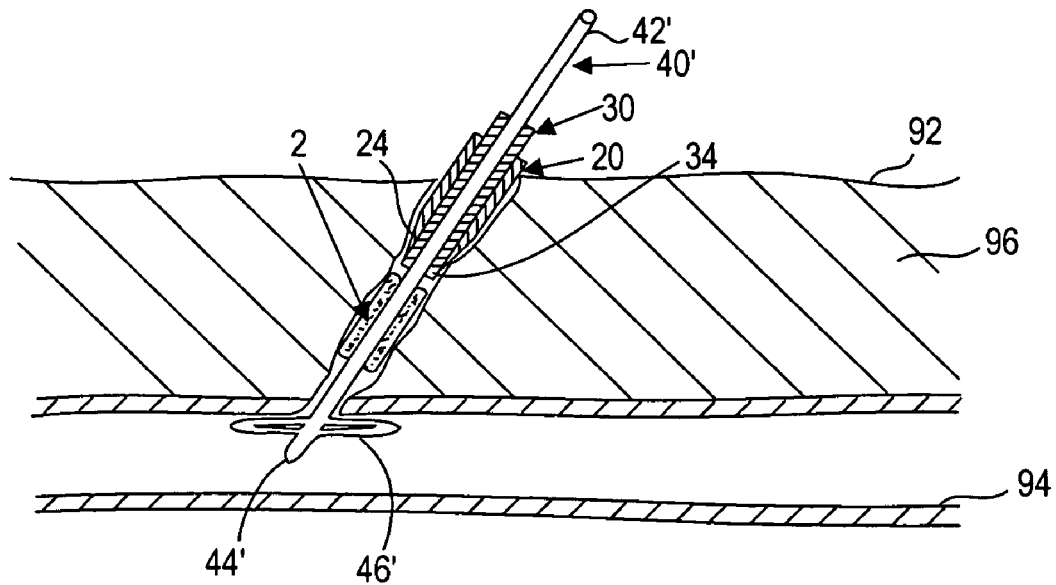

Turning now to FIG. 4D, the plug device 2 may then be deployed from the delivery sheath 20. For example, as described above with respect to FIG. 3, the delivery sheath 20 may include a pusher member 30 within the lumen 26 and disposed proximal to the plug device 2. With the distal end 24 of the delivery sheath 20, and consequently the distal end 16 of the plug device 2, located proximal to the vessel 94, the delivery sheath 20 may be retracted proximally, while maintaining the pusher member 30 substantially stationary. Thus, the pusher member 30 may retain the plug device 2 in position within the puncture 90 while the delivery sheath 20 is retracted from around the plug device 2.

In one embodiment, the plug device 2 may be offset proximally from the distal end 24 of the delivery sheath 20 a predetermined distance, e.g., between about two millimeters (2 mm) and ten millimeters (10 mm), and in an exemplary embodiment, about five millimeters (5 mm), such that the plug device 2 is delivered within the puncture 90 offset proximally from the vessel 94. Alternatively, the plug device 2 may be located immediately adjacent the distal end 24 of the delivery sheath 20.

Alternatively or in addition, the pusher member 30 may be advanced distally relative to the delivery sheath 20 to deliver the plug device 2 into the puncture 90. For example, the pusher member 30 may be advanced until the plug device 2 abuts the positioning element 46 of the positioning member 40. This may ensure that the plug device 2 is delivered adjacent to the vessel 94, providing tactile feedback when the plug device 2 abuts the positioning element 46. Alternatively, as shown in FIG. 5B, if the plug device 2 is disposed within the delivery sheath 20 along with the positioning element 46," the pusher member 30 may be used to deploy the positioning element 46" and plug device 2 sequentially.

Figure 4E:
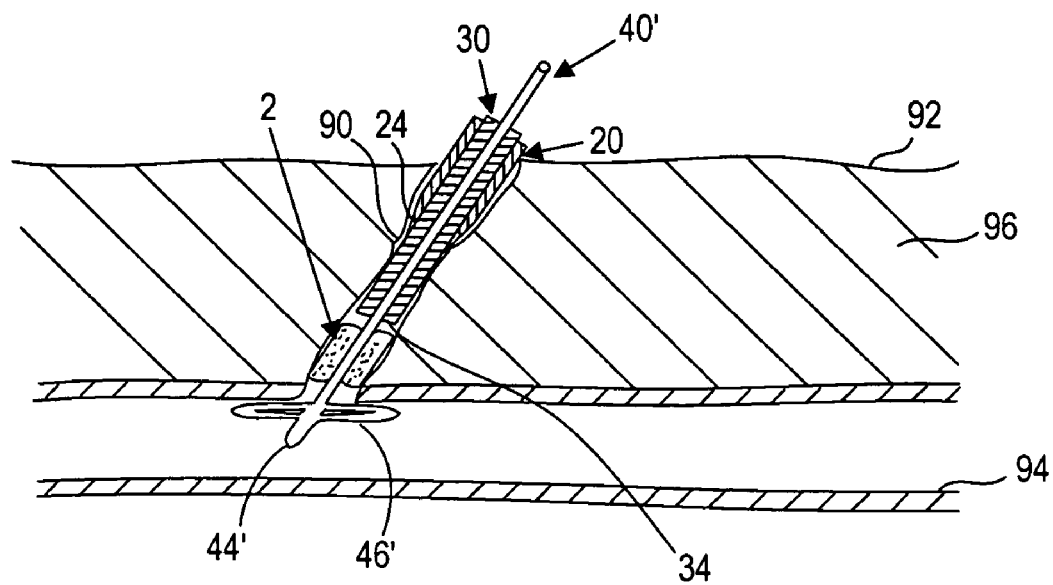

As shown in FIG. 4E, if desired, the pusher member 30 may be used to compress, pack, or cinch the plug device 2 within the puncture 90. For example, after the plug device 2 is exposed within the puncture 90 (e.g., using one of the methods described above), the pusher member 30 may be advanced to push the plug device 2 distally against the positioning element 46.' This may place the distal end 16 of the plug device 2 adjacent to or against the wall of the vessel 94, which may enhance hemostasis in the arteriotomy between the vessel 94 and the puncture 90. Optionally, the pusher member 30 may be advanced further, thereby compressing the plug device 2 axially, which may enhance the plug device 2 expanding radially to fill the puncture 90 and/or permeate outwardly against or into the surrounding tissue.

Optionally, after the plug device 2 is deployed within the puncture 90, additional sealing compound may be delivered into the puncture 90, e.g., to fill all or a portion of the puncture 90 above and/or around the plug device 2. For example, the delivery sheath 20 or the pusher member 30 may be used to deliver liquid sealing compound, e.g., hydrogel precursors (not shown), into the puncture 90, e.g., through the lumen 26 (of the delivery sheath 20) or lumen 36 of the pusher member 30 (or through a separate lumen (not shown) in either device).

In one embodiment, the delivery sheath 20 may include one or more side ports (not shown) on the proximal end of the delivery sheath 20 that may be coupled to a source of sealing compound, such as a syringe assembly storing hydrogel precursors (not shown). If the delivery sheath 20 has not been removed entirely from the puncture 90, the delivery sheath 20 may be advanced into the puncture 90 until the distal end 24 is disposed adjacent the plug device 2, whereupon the sealing compound may be delivered into the puncture 90.

Alternatively, the delivery sheath 20 may be retracted as the sealing compound is delivered, e.g., to at least partially fill the puncture 90. In a further alternative, e.g., if the delivery sheath 20 has been removed, the pusher member 30 may be used to deliver sealing compound in a similar manner to those just described. In still another alternative, a separate sheath or other delivery device (not shown) may be introduced into the puncture 90 to deliver the liquid sealing compound above and/or around the plug device 2. Exemplary apparatus and methods for delivering such sealing compounds into the puncture 90 are disclosed in co-pending application Ser. Nos. 10/454,362 and 10/806,952, filed Mar. 22, 2004, the entire disclosures of which are expressly incorporated by reference herein.

Figure 4F:
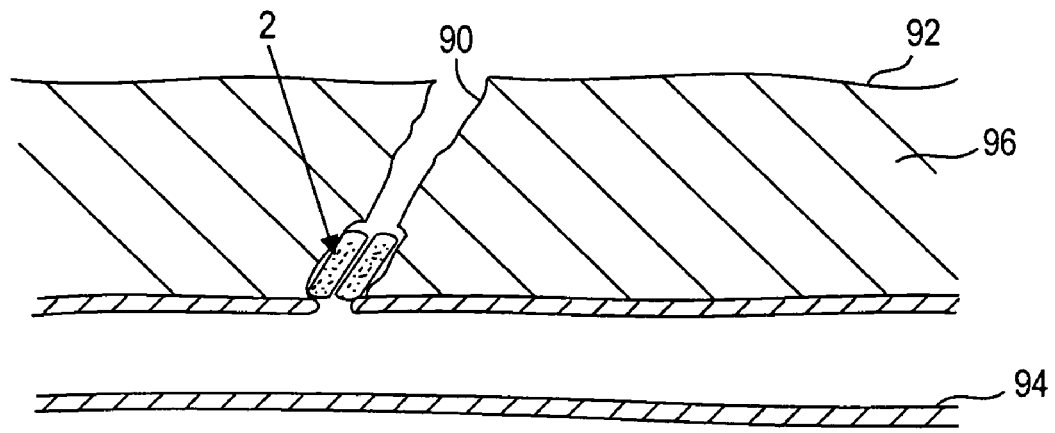

Turning to FIG. 4F, the positioning member 40, pusher member 30, and the delivery sheath 20 (if the distal end 24 still extends into the puncture 90) may then be removed, leaving the plug device 2 within the puncture 90. The components of the apparatus 1 may be removed in any desired order. For example, in one method, the positioning member 40 may be withdrawn through the plug device 2 and the lumen 36 of the pusher member 30. The pusher member 30 may restrain the plug device 2 from moving proximally as the positioning member 40 is removed. Once the positioning member 30 is removed, the pusher member 30 (and the delivery sheath 20, if not already removed) may then be removed.

Alternatively, the delivery sheath 20 and pusher member 30 may be withdrawn first followed by the positioning member 40. In yet another alternative, the positioning element, such as the foot plate 46" may remain within the vessel 94 after the plug device 2 is delivered. In this alternative, the foot plate 46" (or other positioning element) may be made at least partially from a bioabsorbable material, e.g., a relatively fast absorbing material, such as that disclosed in co-pending application Ser. No. 10/928,744, filed Aug. 27, 2004, entitled "Apparatus and Methods for Facilitating Hemostasis within a Vascular Puncture", the entire disclosure of which is expressly incorporated herein by reference.

If the positioning member 40 is removed, the positioning element 46 may be collapsed to allow the positioning member 40 to be removed through the lumen 10 of the plug device 2 without substantially moving or disrupting the plug device 2. For example, a sleeve or other constraint (not shown) may be advanced over the positioning member 40 until it contacts and forces the positioning element 46 to collapse as it enters the sleeve. Alternatively, if the positioning element 46 is controlled by an actuator (not shown), the actuator may be manipulated to collapse the positioning element 46 before the positioning member 40 is removed. In another alternative, the positioning member 40 may simply be pulled proximally until the positioning element 46 contacts the plug device 2 and forces the positioning element 46 to collapse as it enters the lumen 10 of the plug device 2.

With the positioning element 46 collapsed, blood and/or other fluid within the vessel 94 may enter the puncture 90, thereby exposing the plug device 2 to an aqueous physiological environment. The aqueous physiological environment, which may include blood or other bodily fluids from the vessel 94 (or other body lumen) may wet the plug device 2, thereby initiating a reaction between the first and second precursors thereon. For example, the fluid may dissolve the activating agent 8, changing the pH of the fluid to initiate the first and second hydrogel precursors 6, 8 reacting with one another. The reaction of the first and second hydrogel precursors 6, 7 may form an adhesive or "sticky" hydrogel coating 38 that may bond or otherwise attach to tissue surrounding the puncture 90, which may facilitate retaining the plug device 2 in place within the puncture 90. In addition, the hydrogel coating 38 may also expand or swell to further aid in retaining the plug device 2 within the puncture 90 and/or enhance sealing the puncture 90. It will be appreciated that, although hydrogel precursors are described herein, other multiple component adhesives and/or reactive components may be applied to the carrier 4 to create an adhesive or other coating around the carrier 4 when the plug device 2 is exposed to fluid within the patient's body.

Optionally, upon reaction of the first and second hydrogel precursors 6, 7, the porous carrier 4 may be exposed to an aqueous physiological environment, e.g., blood within the puncture 90, e.g., as the first and second precursors 6, 8 dissolve and/or react. Thus, if the carrier 4 includes prothrombotic material, the material may cause and/or accelerate coagulation of the blood within the puncture 90, thereby enhancing hemostasis. Optionally, as the carrier 4 contacts blood, the carrier 4 may expand to substantially occlude the lumen 10, although alternatively, the lumen 10 may be sufficiently small to seal by natural hemostasis of the blood. In addition, if the carrier 4 includes therapeutic and/or pharmaceutical agent(s), the blood and/or surrounding tissue may become exposed to the agent(s), thereby enhancing hemostasis, patient comfort, healing, and the like.

Turning to FIGS. 6A-6C, another embodiment of a plug device 102 is shown for sealing a puncture extending through tissue (not shown). Generally, the device 102 includes a carrier or core 104, e.g., in a predetermined shape. The carrier 104 is formed from a lyophilized (i.e., freeze-dried) PEG polymer that contains hydrolytically degradable chemical groups. While FIGS. 6A and 6B illustrate a carrier 104 in the shape of a cylindrical plug having proximal and distal ends 114, 116, it will be appreciated that the carrier 104 may have other cross-sections or shapes, such as elliptical, triangular, square, conical, disk, polygonic shapes, etc. (not shown).

In one embodiment, the carrier 104 is formed from a lyophilized PEG polymer without any surface adherent layer or sticky coating. In this embodiment, the carrier 104 or plug device 102 may be secured within a puncture simply due to expansion of the carrier 104 within the puncture, e.g., upon exposure to blood or other bodily fluids. The lyophilized PEG polymer, e.g., including a macroporous polymer network, may uptake fluid and expand when exposed to an aqueous environment. The magnitude of expansion or swelling (pre to post hydration) may be significant, e.g., between about two and ten times (2×-10×) its lyophilized size based on volume. In addition or alternatively, the lyophilized hydrogel may absorb between about two and ten times its weight in liquid, causing the carrier 104 to expand substantially. The hydrogel may absorb liquid until it is substantially saturated, e.g., within a few minutes, e.g., not more than about two minutes.

Optionally, with additional reference to FIGS. 6B and 6C, a surface adherent layer or coating 106 may be provided on all or a portion of the carrier 104. For example, the adherent layer 106 may be a mixture of un-cross-linked PEG polymers, similar to the previous embodiments, including first and second PEG polymers 107 in an initially unreactive state and admixed with a pH adjusting agent 108. In an exemplary embodiment, the first PEG polymer may be formed from an amine-terminated PEG polymer while the second PEG polymer may be formed from an ester-terminated, hydrolytically degradable PEG polymer.

The first and second PEG polymers 107 may include any number of PEG polymer precursor materials, such as those disclosed in U.S. Pat. Nos. 6,152,943, 6,165,201, 6,179,862, 6,514,534, 6,379,373, 6,703,047, and in co-pending application Ser. Nos. 10/010,715 filed Nov. 9, 2001, Ser. No. 10/068,807 filed Feb. 5, 2002, and Ser. No. 10/454,362, filed Jun. 4, 2003, the disclosures of which are incorporated by reference above. The pH adjusting agent 108 may include, for example, sodium borate, such as $Na_2B_4O_7 \cdot 10H_2O$ in crystalline or powder form, similar to the previous embodiments, sodium bicarbonate, or other salt-based materials, and the like that may alter the localized pH on or around the carrier 104.

The first and second PEG polymers 107 and pH adjusting agent 108 may be carried on all or a portion of the carrier 104, e.g., dispersed on an outer surface or within the carrier 104. In particular, the first and second PEG polymers 107 may remain in the unreactive state, e.g., before or until exposure to an aqueous physiological environment, which may exist, for example, inside a puncture or other passage through tissue.

Blood or other bodily fluids that contact the PEG polymer-laden carrier 104 may initiate a cross-link forming reaction between the two PEG polymers 107 carried in the adherent layer 106. The reaction of the PEG polymers 107 may create a cross-linked adhesive or tacky hydrogel, which may aid in retaining the plug device 102 within a puncture after deployment and/or in facilitating hemostasis within the puncture. The cross-linking reaction may occur, for example, when the plug device 104 is in intimate contact with tissue surrounding the puncture, such as fat cells within the fascia or other tissue layers.

This cross-linking reaction may mechanically lock or otherwise secure the plug device 102 within the puncture, e.g., to maintain its position post-deployment. This securing property may be particularly advantageous in situations where the patient will ambulate shortly after completing the procedure, which otherwise may increase the potential of plug migration and, consequently, of bleeding complications. By substantially securing the plug device 102 in place locally within the puncture, the target deployment location may be maintained within the patient while the puncture site heals.

In addition, the lyophilized PEG polymer forming the carrier 104 may hydrate rapidly after contacting blood or other bodily fluids. Consequently, any blood or other bodily fluid that leaks from the puncture site and/or surrounding tissue before significant degradation of the carrier 104 may immediately re-trigger the hydration reaction of the carrier 104 material, thereby improving the potential for puncture closure.

The material of the plug device 102, i.e., the carrier 104 and/or adherent layer 106, may be at least partially absorbed by the body over time, e.g., over a period of days, weeks, or months. Optionally, the carrier 104 and/or adherent layer 106 may include therapeutic and/or pharmaceutical agents, e.g., to promote healing, prevent infection and/or other adverse medical events, and the like. Such agents may be embedded in the carrier material and/or adherent layer 106 and/or applied as one or more coatings or layers. In addition, the material of the carrier 104 may have a substantially uniform composition or the composition may be varied, e.g., along its length and/or within underlying layers within the carrier 104.

Returning to FIGS. 6A and 6B, in the embodiment shown, the carrier 104 includes proximal and distal ends 114, 116, and a lumen 110 extending between the proximal and distal ends 114, 116, thereby defining a longitudinal axis 118. The lumen 110 may be created when the carrier 104 is formed, e.g., if the carrier 104 is rolled from one or more sheets or layers of material or formed by molding. Alternatively, the lumen 110 may be formed by boring into or otherwise removing material from an already formed solid carrier 104. The lumen 110 may be dimensioned and/or sized for receiving a catheter, guide wire, or other elongate member, therethrough. For example, as described further below, a portion of a positioning member 140 may slide or otherwise pass through the lumen 110 of the carrier 104, e.g., while delivering the plug device 102.

The shape of the lyophilized PEG polymer forming the carrier 104 may be fixed at the time of lyophilization. Alternatively, the lyophilized PEG polymer may be formed in various pre-formed shapes, such as sheets and/or blocks, which may then be formed post-dehydration into a desired geometry, e.g., to facilitate placement within a delivery system, such as the apparatus 101 described below. Various shaping/sizing processes may be employed to transform the lyophilized PEG polymer into the desired size and/or geometry, such as die cutting, rolling, flattening, compression molding, and the like.

FIG. 6B illustrates the carrier 104 loaded with a mixture of first and second PEG polymers 107 and a pH adjusting agent 108. In one embodiment, a powdered form of an amine-terminated polymer may be used as the first PEG polymer while an ester terminated, hydrolytically degradable PEG polymer in powder form is used as the second PEG polymer, similar to the previous embodiments. Unlike the previous embodiments, the two powders may be mixed in a mixing container while in powder form. Powdered sodium borate crystals, e.g., milled into a fine powder to reduce granularity and to better enable mixing, may be added to the first and second PEG polymer 107 mixture.

The resulting mixture (first and second PEG polymers 107 and pH adjusting agent 108) may then be heated to about 40° C. to melt the first and second PEG polymers 107 and/or the pH adjusting agent 108. The melted mixture is preferably thoroughly mixed, e.g., to ensure a substantially uniform or otherwise desired distribution of the constituents.

The melted mixture (first and second PEG polymers 107 and pH adjusting agent 108) may then be applied to all or a portion of an exposed surface of the carrier 104. The mixture may be applied by any number of methods, for example, by painting the heated liquid mixture onto the carrier 104 with a brush or other applicator, by spraying an aerosol of the heated liquid mixture onto the carrier 104, or by dipping or wicking the heated liquid mixture onto the carrier 104 using a bath and the like containing the heated liquid mixture. Once the heated liquid mixture has been sufficiently applied to the carrier 104, the mixture may be allowed to cool, e.g., to solidify and/or otherwise form the adherent layer 106. After cooling, a solid or semi-solid adherent layer 106 may surround the lyophilized carrier 102.

In one embodiment, the proximal end 114 and distal end 116 of the carrier 104 are not covered with an adherent layer 106, as shown in FIG. 6B. In this regard, the lyophilized PEG polymer at the proximal and distal ends 114, 116 of the carrier 104 may remain exposed, e.g., to facilitate subsequent hydration. This particular embodiment has excellent swelling/expansion characteristics, while substantially maintaining the position of the plug device 102 at a desired target location.

FIG. 6C shows a magnified cross-sectional view of the exterior surface of the adherent layer 106 disposed on an exposed surface of a lyophilized carrier 104. As shown, the first and second PEG polymers 107, as well as the pH adjusting agent 108, are all well mixed within the entire adherent layer 106. Alternatively, the relative concentration of the components of the adherent layer 106 may vary along the carrier 104.

Figure 7:
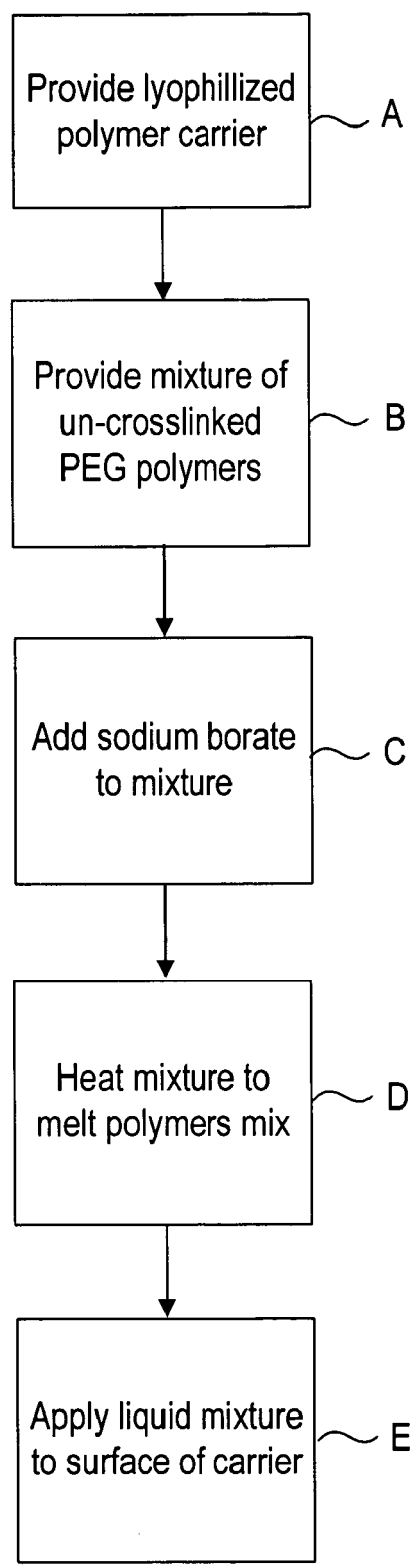
FIG. 7 is a flowchart showing a method for providing an adherent "sticky" layer on a lyophilized carrier.

Turning to FIG. 7, an exemplary method is shown for making a sealing device, such as plug device 102 described above. First, at step A, a lyophilized polymer carrier 104 is provided, e.g., by forming a plug or other body from a PEG polymer that contains hydrolytically degradable chemical groups. As described above, the carrier 104 may be formed by rolling one or more sheets of material into a desired shape, by molding, by cutting individual devices from a larger mass of material, machining, grinding, and the like.

Next, at step B, a mixture of first and second PEG polymers 107 (uncross-linked) is provided in a predetermined ratio, e.g., in an equimolar ratio. Next, at step C, a pH activating agent 108, such as solid sodium borate, may be added to the mixture created in step B. In one embodiment, the pH activating agent 108 is milled into a fine powder before being added to the mixture of first and second PEG polymers 107. At step D, the resulting mixture formed in step C may then be heated to a predetermined temperature to melt the first and second PEG polymers 107. In one embodiment, the mixture is heated to a temperature of about forty degrees Celsius (40° C.). After the first and second PEG polymers 107 have melted (while the borate crystals remain solid), the entire mixture may be thoroughly mixed.

At step E, the heated liquid mixture may then be applied to the carrier 104, e.g., to one or more exposed surfaces of carrier 104 using one of the methods described above, to form the adherent layer 106. In an alternative embodiment, the first and second precursors may be dissolved in one or more solvents that allow the precursors to be mixed and/or applied to the carrier 104, while remaining in an unreactive state relative to one another, e.g., methylene chloride, dimethyl sulfoxide, hot acetone, and the like. Optionally, one or more therapeutic and/or pharmaceutical agents may be applied to the carrier 104 and/or adherent layer 106. Alternatively, the adherent layer 106 may be applied or otherwise dispersed within the carrier 104, e.g., by dipping or wicking or by creating multiple layers for the carrier 104 that are coated and successively formed together to create the final carrier 104.

In alternative embodiments, other laminate structures may be provided for the plug device 102. For example, a sheet including multiple layers of different components, such as one or more of the components described above, may be formed, and the sheet may be rolled into a tubular or solid cylindrical structure. An exemplary embodiment of such a sheet may include three layers, e.g., a first layer of lyophilized hydrogel, a second layer of two-part hydrogel adherent material, and a third layer of lyophilized hydrogel. Thus, in this embodiment, the adherent layer, e.g., including two hydrogel precursors in an initially unreactive state, may be sandwiched between layers of lyophilized hydrogel.

In another embodiment, a layer of lyophilized hydrogel may be provided, and an adherent layer, e.g., including two hydrogel precursors in an initially unreactive state, may be applied to one surface of the layer of lyophilized hydrogel. A pH adjusting agent, e.g., borate crystals, may be embedded or otherwise applied to the opposite surface of the layer of lyophilized hydrogel. Thus, in this embodiment, the pH adjusting agent may be substantially segregated from the adherent layer. This may be desirable to prevent the pH adjusting agent from initiating reaction of the materials of the adherent layer prematurely, which may otherwise occur to some degree, even absent an aqueous environment. The resulting composite material may then be folded or rolled into a desired plug configuration.

Turning to FIGS. 8 and 9A-9D, a delivery apparatus 101 is shown for sealing a puncture 90 through tissue 96, e.g., to a vessel 94 or other body lumen, similar to the previous embodiments. Generally, the apparatus 101 includes an introducer or delivery sheath or other tubular member 20 and a positioning member 140, e.g., similar to the previous embodiments. The delivery apparatus 101 also includes a cartridge 120 carrying a plug device 102, such as one of those described above, and a plunger, cincher, or other pusher member 130.

Figure 8:
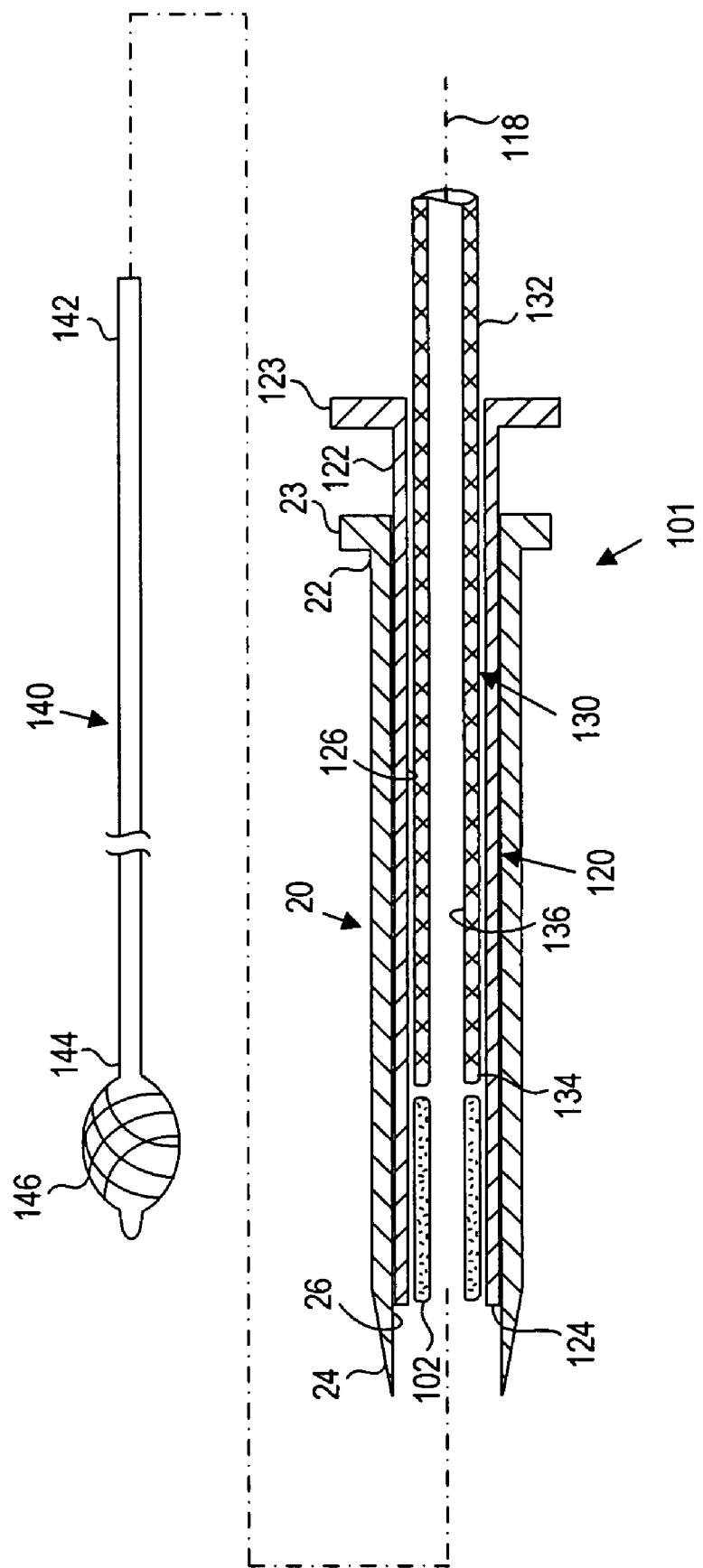
FIG. 8 is an exploded side view of an apparatus for delivering a plug device into a puncture through tissue.

The cartridge 120 generally includes an elongate tubular body including a proximal end 122, a distal end 124, and a lumen 126 extending between the proximal and distal ends 122, 124 within which the plug device 102 may be carried. The pusher member 130 may also be an elongate tubular body including a proximal end 132, a distal end 134, and a lumen 136 extending between the proximal and distal ends 132, 134. The positioning member 140 may include an elongate member having a proximal end 142, a distal end 144, and an expandable positioning element 146 on the distal end 144, such as an expandable mesh (as shown in FIG. 8), a mechanically expandable structure, or a balloon (not shown).

The delivery apparatus 101 may be used to position and deliver the plug device 102 within a puncture 90, e.g., extravascularly just above or otherwise adjacent to the arteriotomy in a vessel 94 communicating with the puncture 90. In one embodiment, the cartridge 120 may be insertable or otherwise slidable within lumen 26 of the delivery sheath 20, and the pusher member 130 may be slidable within the lumen 126 of the cartridge 120. The plug device 102 may be compressed or otherwise disposed within the lumen 126 of the cartridge 120 distal to the pusher member 130. The positioning member 140 may insertable through the cartridge 120, e.g., through the pusher member 130 and plug device 102.

Thus, the plug device 102 may be disposed between an inner wall of the cartridge 120 and an exterior surface of the positioning member 140. As explained below, the cartridge 120 may be used to shuttle the plug device 102 into position for deployment, i.e., through the delivery sheath 20. The pusher member 130 may be positioned proximal to the plug device 102 for positioning and/or maintaining the plug device 102 in a predetermined location during deployment.

Figure 9A:
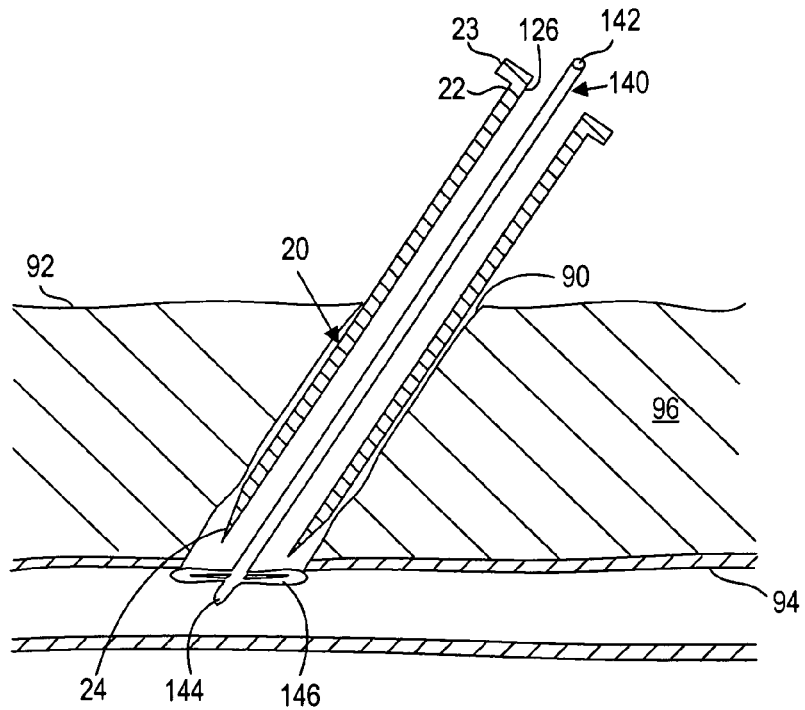
FIGS. 9A-9D are cross-sectional views of a patient's body, showing a method for sealing a puncture extending from the patient's skin to a blood vessel using the apparatus of FIG. 8.

With reference to FIGS. 9A-9D and 10A-10B, the delivery apparatus 101 may be used to deliver the plug device 102 and/or otherwise facilitate hemostasis within a puncture 90 through tissue 94. Initially, delivery sheath 20 may be placed within the puncture 90, e.g., to provide access to vessel 94, similar to the previous embodiments. With reference to FIG. 9A, a positioning member 140 may be introduced into and/or through the lumen 26 of the delivery sheath 20, e.g., with the expandable frame or other positioning element 146 thereon in a collapsed condition.

Figure 10A:
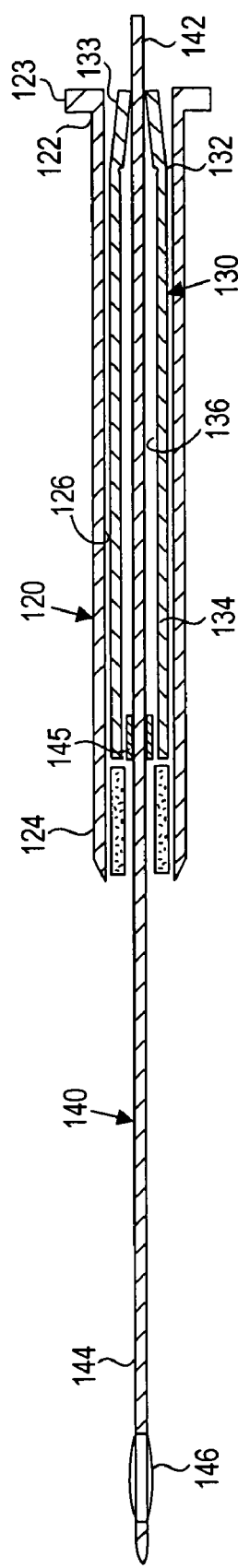
FIGS. 10A and 10B are cross-sectional views of another embodiment of an apparatus for delivering a plug device into a puncture through tissue.

The cartridge 120 (along with the plug device 102 and pusher member 130) may be provided initially on the proximal end 142 of the positioning member 140, as shown in FIG. 10A. Thus, the cartridge 120 may initially be located outside the puncture 90 as the positioning member 130 is advanced into the puncture 90. Alternatively, the cartridge 120 may be carried on the distal end 144 of the positioning member 140, e.g., such that the cartridge 120 (along with the plug device 102 and pusher member 130) are introduced simultaneously with the positioning member 140. In a further alternative, the cartridge 120 may be provided separate from the positioning member 140. When the positioning member 140 is advanced into the puncture 90, the shaft of the positioning member 140 may extend proximally from the proximal end 22 of the delivery sheath 20, and may be later back-loaded into the cartridge 120, e.g., through the lumen 136 of the pusher member 130 and/or the lumen 110 of the plug device 102.

Still referring to FIG. 9A, the distal end 144 of the positioning member 140 may be inserted through the puncture 90 and the arteriotomy into the vessel 94. The positioning element 146 on the distal end 144 of the positioning member 140 may be expanded or otherwise deployed, similar to the previous embodiments. As shown in FIG. 9A, the expandable positioning element 146 on the positioning member 140 may be mechanically expanded or inflated to an enlarged condition.

After expanding the positioning element 146, the positioning member 140 may be at least partially withdrawn until the positioning element 146 contacts the wall of the vessel 94, e.g., to substantially seal the vessel 94 from the puncture 90. This may involve a two-step, tactile process, similar to the previous embodiments, in which the positioning member 140 with expanded positioning element 146 is withdrawn until it contacts the distal end 24 of the delivery sheath 20 and then until the positioning element 146 contacts the wall of the vessel 94. Tension in the proximal direction may be applied and/or maintained on the positioning member 140 to retract the positioning element 146, e.g., to seal the puncture 90. The proximal tension may be maintained manually or using a tensioner device (not shown), such as that disclosed in application Ser. No. 10/806,952 incorporated by reference above, to provide temporary hemostasis, e.g., during the subsequent steps.

Figure 9B:
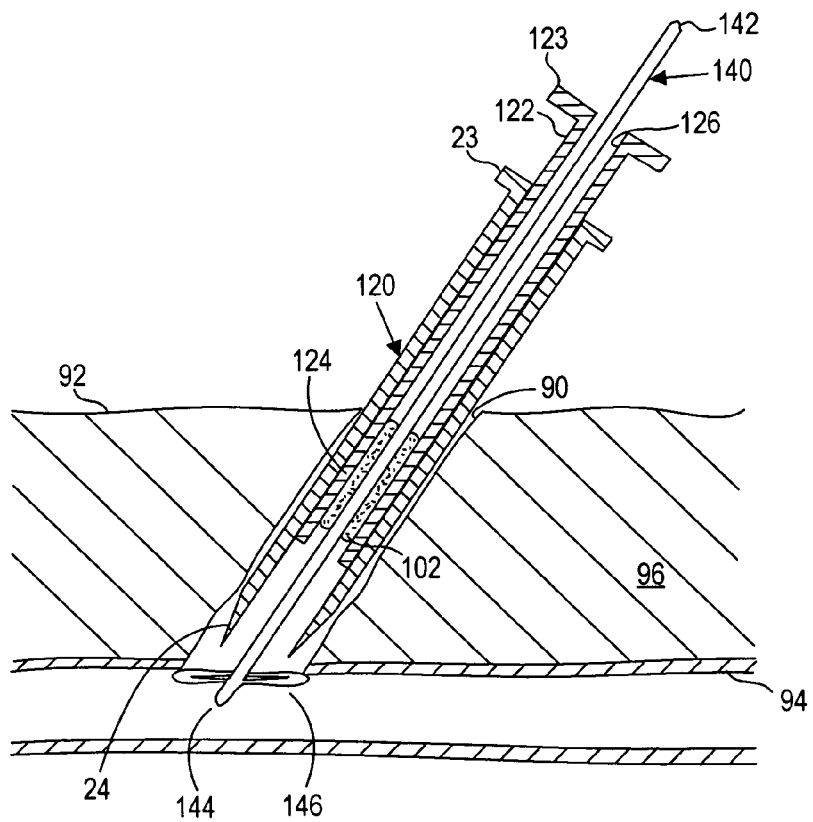

Turning to FIG. 9B, the cartridge 120 carrying the plug device 102 may be advanced distally over the positioning member 140 into the puncture 90. In one embodiment, the cartridge 120 (and plug device 102) may be advanced through the delivery sheath 20 until a hub 123 of the cartridge 120 abuts a hub 23 on the delivery sheath 20 (shown in FIG. 9C). Optionally, the positioning member 140 and/or pusher member 130 may include one or more cooperating detents that may engage when the cartridge 120 reaches a predetermined location along the positioning member 140, e.g., to limit subsequent movement of the pusher member 130 relative to the positioning member 140.

Figure 10B:
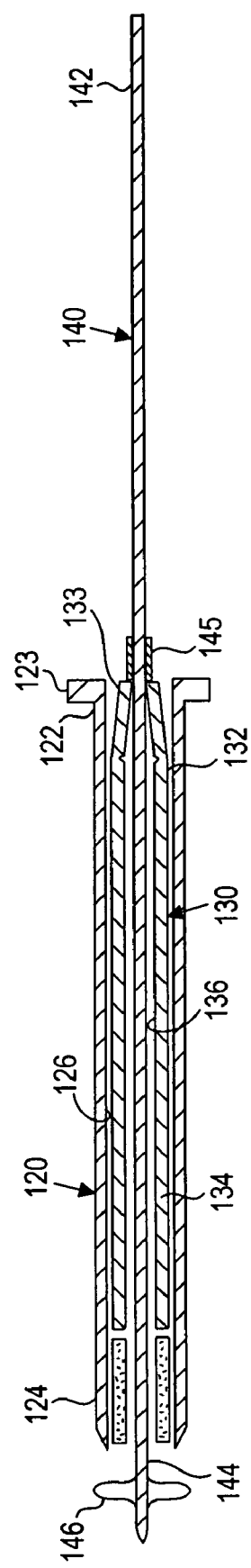

For example, as shown in FIGS. 10A and 10B, the positioning member 140 may include a ring, tab, or other raised element 145, and the pusher member 130 may include a living hinge, tab, or other latch element 135, e.g., on proximal end 132. For example, the latch element 135 may simply be an annular notch in the proximal end 132 of the pusher member 130 to bias the proximal end inwardly. As the cartridge 120 (and consequently the pusher member 130) is advanced, the latch element 135 that may pass freely over the raised element 145. The latch element 135 then may prevent the pusher member 130 from being retracted again, the blunt edge of the latch element 135 abutting the ring 145 on the positioning member 140.

Alternatively, the cartridge member 120 and pusher member 130 may be provided initially on the positioning member 140, as shown in FIG. 10B. In this alternative, the pusher member 130 and positioning member 140 may include the cooperating detents 133, 145 to prevent proximal movement of the pusher member 130 relative to the positioning member 140. Alternatively, the pusher member 130 may be otherwise fixed relative to the positioning member 140, e.g., to fix the distal end 134 of the pusher member 130 a predetermined distance proximal to the positioning element 146, e.g., to position the plug device 102 immediately adjacent the positioning element 146, as shown in FIG. 10B. While advanced into the delivery sheath 20 or otherwise within the puncture 90, the plug device 102 may remain out of direct or indirect contact with blood or other bodily fluids along the blood path.

Figure 9C:
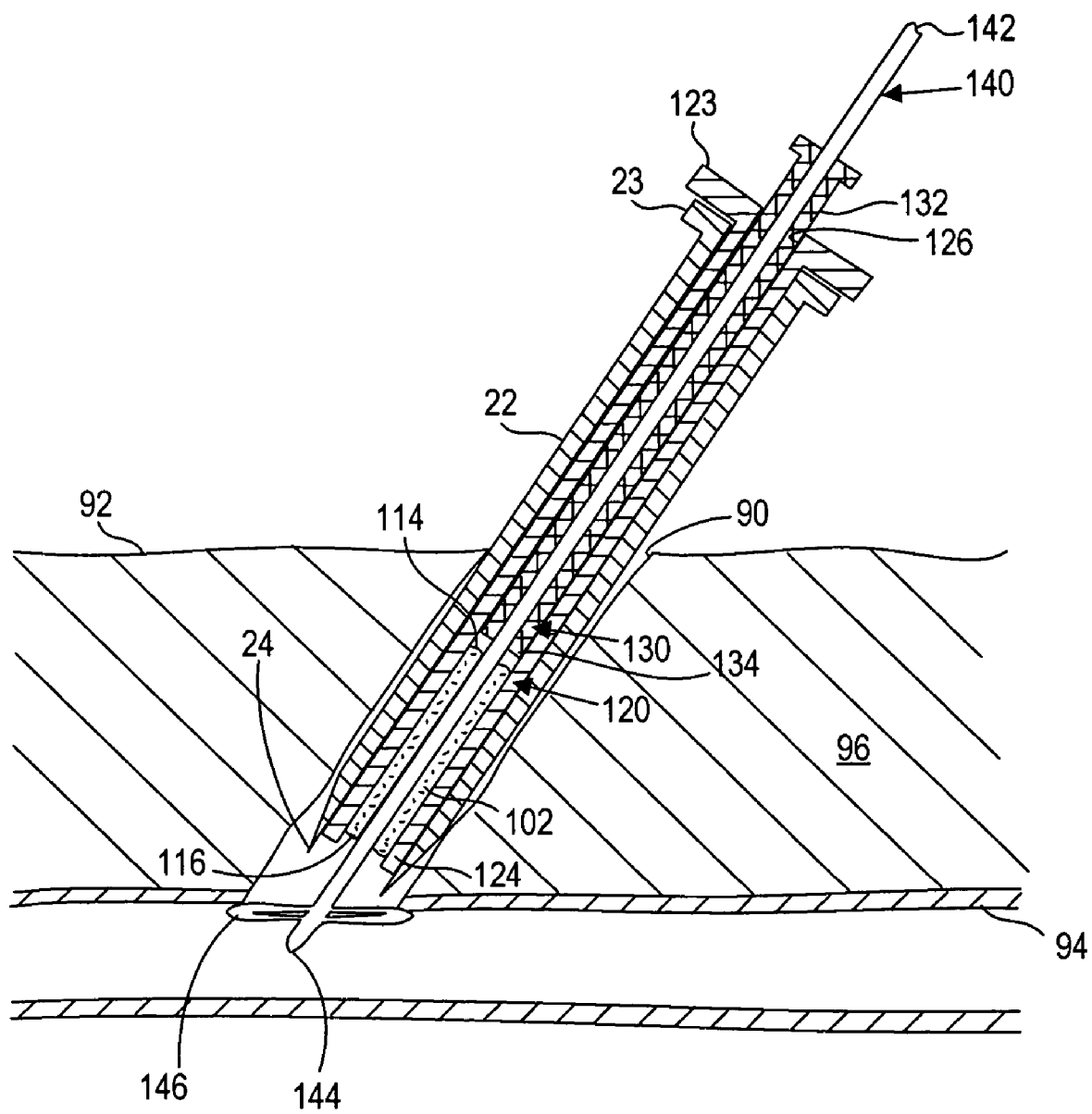

Now referring to FIG. 9C, if the pusher member 130 is not already provided within the cartridge 120, the pusher member 130 may be advanced distally into the lumen 126 of the cartridge 120, e.g., until a marker 137 on the pusher member 130 is located adjacent to the hub 123 of the cartridge 120. As seen in FIG. 9C, this marker location may place the distal end 134 of the pusher member 130 proximally adjacent to the proximal end 114 of the plug device 102. Alternatively, the pusher member 130 and plug device 102 may be initially positioned within the cartridge 120 as shown in FIG. 9C, i.e., with the plug device 102 adjacent the distal end 124 the cartridge 120, thereby eliminating the need to advance the pusher member 130.

Figure 9D:
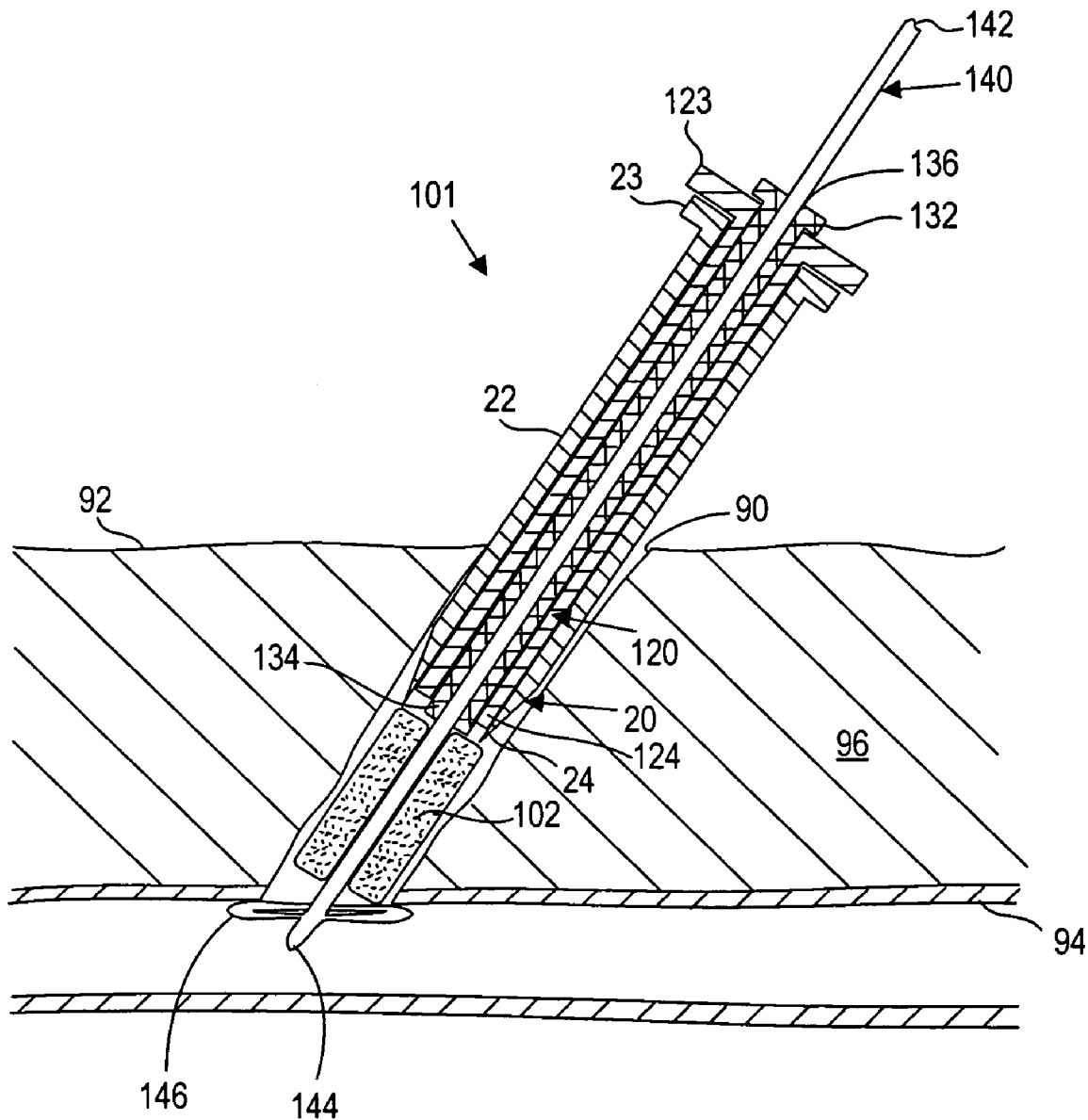

Next, as shown in FIG. 9D, while proximal tension on the positioning member 140 is used to seal the vessel 94 from the puncture 90, the position of the pusher member 130 is maintained, and the delivery sheath 20 and cartridge 120 are retracted proximally to expose or otherwise deploy the plug device 102 within the puncture 90. The pusher member 130 may serve as a stop that prevents the plug device 102 from moving proximally while the delivery sheath 20 and cartridge 120 are withdrawn.

In one embodiment, the user of the delivery apparatus 101 may position his or her thumb on hub 133 of the pusher member 130 to maintain its position while the delivery sheath 20 and cartridge 120 are retracted, e.g., using his or her index and middle fingers. For example, as shown in FIG. 9D, where the hub 123 of the cartridge 120 abuts the hub 23 of the delivery sheath 20, the delivery sheath 20 may be held and withdrawn, thereby causing the cartridge 120 to be withdrawn simultaneously. Alternatively, the cartridge 120 may be removed first, and then the delivery sheath 20 may be removed. The cartridge 120 and delivery sheath 20 may be removed entirely from the puncture 90 or only to expose the plug device 102.

Optionally, the plug device 102 may be tamped or otherwise compressed within the puncture 90, e.g., by advancing the pusher member 130 distally to press the plug device 102 against the wall of the vessel 94 and/or against the positioning element 146, similar to the previous embodiments. This may cinch the plug device 102, which may cause the plug device 102 to expand radially outwardly and/or press the plug device 102 against the arteriotomy, e.g., to enhance sealing the puncture 90 from the vessel 94.

After delivering the plug device 102, the proximal tension on the positioning member 140 may be released and/or the positioning element 146 may be collapsed to its collapsed state. For example, the positioning element 146 may be mechanically collapsed or deflated. After the positioning element 146 is collapsed, the positioning member 140 (and consequently the positioning element 146) may be slowly withdrawn through the lumen 110 of the plug 102.

In an exemplary embodiment, the positioning element 146 may have a profile not more than about 0.875 millimeter (035 inch) to facilitate removal of the positioning member 140 without substantially disturbing the deployed plug device 100. While the positioning member 140 is withdrawn, the pusher member 130 may be maintained to serve as a stop and prevent proximal migration of the plug device 102 within the puncture 90. In addition, in embodiments where the plug device 102 includes an adherent layer (not shown in FIG. 9D), the "sticky" adherent layer may also aid in securing the plug device 102 to the surrounding tissue.

After removing the positioning member 140, the pusher member 130 may be withdrawn, leaving the plug device 102 in place. If desired, e.g., if bleeding occurs proximally through the lumen 136 of the pusher member 130, liquid hydrogel or other sealing compound may be delivered into the puncture 90 above and/or around the plug device 102, similar to the previous embodiments, to assist in achieving permanent hemostasis. For example, a source of sealing compound (not shown) may be coupled to the proximal end 132 of the pusher member 130 and sealing compound may be delivered into the puncture above and/or around the plug device 102.

Optionally, the pusher member 130 may be retracted proximally as the sealing compound is delivered to at least partially fill the puncture 90 with the sealing compound While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. An apparatus for sealing a puncture extending through tissue, comprising:
    a tubular member comprising a proximal end, a distal end sized for insertion through the puncture, a lumen extending between the proximal and distal ends, and a distal opening in communication with the lumen;
    a plug disposed within the lumen, the plug comprising first and second precursors disposed on at least a portion of an exterior of a core, the first and second precursors remaining in an unreactive state prior to exposure to an aqueous physiological environment in the tissue whereupon the first and second precursors react to form an adhesive around the core; and
    a pusher member slidable within the lumen of the tubular member for deploying the plug through the lumen and out the distal opening of the tubular member.

2. The apparatus of claim 1, wherein the plug comprises a lumen extending between proximal and distal ends thereof, the apparatus further comprising an elongate positioning member, the positioning member having an expandable element on a distal end thereof, the positioning member sized for passing through the lumen of the tubular member and the lumen of the plug.

3. The apparatus of claim 1, further comprising an activating agent disposed on at least a portion of the exterior of the core, the activating agent facilitating or initiating reaction of the first and second precursors when exposed to an aqueous physiological environment.

4. The apparatus of claim 3, wherein the first and second precursors comprise hydrogel precursors, and wherein the activating agent comprises a pH activating agent that modifies a pH of the aqueous physiological environment to initiate the reaction of the first and second hydrogel precursors.

5. The apparatus of claim 4, wherein the pH activating agent comprises a plurality of particles on the exterior surface of the core.

6. The apparatus of claim 1, wherein the core comprises an elongate body having a disk shape, a solid cylindrical shape, a rolled sheet cylindrical shape, or a folded sheet cylindrical shape.

7. An apparatus for sealing a puncture extending through tissue and communicating with a body lumen, comprising:
    a tubular member comprising a proximal end, a distal end sized for insertion through the puncture and into the body lumen, a lumen extending between the proximal and distal ends, and a distal opening communicating with the tubular member lumen, the tubular member defining a longitudinal axis;
    a plug positioned within the lumen and comprising first and second precursors disposed on a core, the first and second precursors remaining in an unreactive state prior to exposure to an aqueous physiological environment, the first and second precursors reacting when exposed to an aqueous physiological environment to form an adhesive on the core, the plug further comprising a lumen extending between proximal and distal ends thereof;
    a pusher member movable within the tubular member lumen for deploying the plug out of the distal opening; and
    an elongate positioning member comprising a proximal end slidable through the plug lumen, and a distal end having a positioning element thereon, the positioning element movable radially away from the longitudinal axis of tubular member within the body lumen for preventing the positioning element from being removed from the body lumen into the puncture.

8. The apparatus of claim 7, wherein the positioning element is disposed within the tubular member lumen in a low profile condition as the tubular member is inserted into the body lumen, the positioning member being movable axially relative to the tubular member for deploying the positioning element within the body lumen, whereupon the positioning element assumes a large profile condition, preventing the positioning element from being removed from the body lumen into the puncture.

9. The apparatus of claim 7, wherein the positioning element comprises a bioabsorbable element that is absorbed after being exposed to fluid within the body lumen.

10. The apparatus of claim 7, wherein the positioning element comprises an expandable structure.

11. The apparatus of claim 7, wherein the plug further includes a pH activating agent disposed on the first and second precursors.

12. The apparatus of claim 7, wherein the core comprises an elongate body having a disk shape, a solid cylindrical shape, or a rolled sheet cylindrical shape.

13. An apparatus for sealing a puncture extending through tissue, comprising:
    a tubular member comprising a proximal end, a distal end sized for insertion through the puncture, a lumen extending between the proximal and distal ends, and a distal opening in communication with the lumen;
    a plug disposed within the lumen;
    a first hydrogel precursor disposed at least partially on an exterior surface of the plug;
    a second hydrogel precursor disposed on the exterior surface of the plug, the first and second precursors remaining in an unreactive state on the plug prior to exposure to an aqueous physiological environment, whereupon the first and second precursors react to form a hydrogel; and
    a pusher member slidable within the lumen of the tubular member for deploying the plug through the lumen and out the distal opening of the tubular member.

14. The apparatus of claim 13, wherein the plug comprises a lumen extending between proximal and distal ends thereof, the apparatus further comprising an elongate positioning member, the positioning member having an expandable element on a distal end thereof, the positioning member sized for passing through the lumen of the tubular member and the lumen of the plug.

15. The apparatus of claim 13, further comprising an activating agent disposed on at least a portion of the exterior of the plug, the activating agent facilitating or initiating reaction of the first and second hydrogel precursors when exposed to an aqueous physiological environment.

16. The apparatus of claim 15, wherein the activating agent comprises a pH activating agent that modifies a pH of the aqueous physiological environment to initiate the reaction of the first and second hydrogel precursors.

17. The apparatus of claim 16, wherein the pH activating agent comprises a plurality of particles on the exterior surface of the plug.

18. The apparatus of claim 13, wherein the plug comprises hydrogel.

19. The apparatus of claim 18, wherein the hydrogel comprises PEG.

20. The apparatus of claim 13, wherein the plug comprises lyophilized or dehydrated hydrogel.

21. The apparatus of claim 13, wherein the first and second hydrogel precursors comprise a coating on at least a portion of the exterior surface of the plug.

22. The apparatus of claim 21, wherein the plug is porous and wherein the first and second hydrogel precursors extend at least partially into pores in the exterior surface of the plug.

23. The apparatus of claim 13, wherein the plug comprises a bio absorbable material.

* * * * *